(12) United States Patent
Ling et al.

(10) Patent No.: US 11,447,731 B2
(45) Date of Patent: Sep. 20, 2022

(54) THREE-DIMENSIONAL BIOREACTORS

(71) Applicant: SOUTHWEST RESEARCH INSTITUTE, San Antonio, TX (US)

(72) Inventors: Jian Ling, Spring Branch, TX (US); Stephen T. Wellinghoff, San Antonio, TX (US); Michael Joseph Rubal, Lytle, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 123 days.

(21) Appl. No.: 16/580,956

(22) Filed: Sep. 24, 2019

(65) Prior Publication Data
US 2020/0157483 A1   May 21, 2020

Related U.S. Application Data

(60) Provisional application No. 62/735,531, filed on Sep. 24, 2018.

(51) Int. Cl.
| | |
|---|---|
| *C12M 1/12* | (2006.01) |
| *C12M 1/00* | (2006.01) |
| *B33Y 80/00* | (2015.01) |
| *C09D 165/04* | (2006.01) |
| *B33Y 10/00* | (2015.01) |

(52) U.S. Cl.
CPC ............. *C12M 23/20* (2013.01); *B33Y 80/00* (2014.12); *C09D 165/04* (2013.01); *C12M 23/02* (2013.01); *C12M 25/14* (2013.01); *B33Y 10/00* (2014.12)

(58) Field of Classification Search
CPC .................................................... C12M 25/14
See application file for complete search history.

(56) References Cited

U.S. PATENT DOCUMENTS

| | | | |
|---|---|---|---|
| 4,247,434 | A | 1/1981 | Vanderhoff et al. |
| 5,360,609 | A | 11/1994 | Wellinghoff |
| 5,443,950 | A | 8/1995 | Naughton et al. |
| 5,631,300 | A | 5/1997 | Wellinghoff |
| 5,639,295 | A | 6/1997 | Wellinghoff et al. |
| 5,650,446 | A | 7/1997 | Wellinghoff et al. |
| 5,668,185 | A | 9/1997 | Wellinghoff et al. |
| 5,695,814 | A | 12/1997 | Wellinghoff et al. |
| 5,705,092 | A | 1/1998 | Wellinghoff et al. |

(Continued)

FOREIGN PATENT DOCUMENTS

| | | |
|---|---|---|
| CA | 2882108 A1 | 3/2014 |
| CA | 3023221 | 11/2019 |

(Continued)

OTHER PUBLICATIONS

Office Action from related Korean Application No. 10-2018-7035015, dated Aug. 30, 2021.

(Continued)

*Primary Examiner* — Jonathan M Hurst
(74) *Attorney, Agent, or Firm* — Grossman, Tucker, Perreault & Pfleger, PLLC

(57) ABSTRACT

The present invention relates to the design, fabrication and applications of three-dimensional (3D) bioreactor for cell expansion and cell secreted substance production. The bioreactors have relatively low levels of potentially cytotoxic compounds, can be coated with substituted or unsubstituted poly(p-xylene) type coatings and can also be separately formed from liquid crystal photopolymerizable monomers.

20 Claims, 25 Drawing Sheets

(56) References Cited

U.S. PATENT DOCUMENTS

| | | |
|---|---|---|
| 5,707,739 A | 1/1998 | Wellinghoff et al. |
| 5,888,528 A | 3/1999 | Wellinghoff et al. |
| 5,914,120 A | 6/1999 | Wellinghoff et al. |
| 5,922,776 A | 7/1999 | Wellinghoff et al. |
| 6,046,243 A | 4/2000 | Wellinghoff et al. |
| 6,277,408 B1 | 8/2001 | Wellinghoff et al. |
| 6,605,304 B1 | 8/2003 | Wellinghoff et al. |
| 7,041,234 B2 | 5/2006 | Wellinghoff et al. |
| 7,094,360 B2 | 8/2006 | Wellinghoff et al. |
| 7,098,359 B2 | 8/2006 | Wellinghoff et al. |
| 7,108,801 B2 | 9/2006 | Wellinghoff et al. |
| 7,147,800 B2 | 12/2006 | Wellinghoff et al. |
| 7,238,831 B2 | 7/2007 | Wellinghoff et al. |
| 7,273,567 B1 | 9/2007 | Wellinghoff et al. |
| 7,678,572 B2 | 3/2010 | Har-Noy |
| 7,956,164 B2 | 6/2011 | Har-Noy |
| 8,007,823 B2 | 8/2011 | Favis et al. |
| 8,012,750 B2 | 9/2011 | Har-Noy |
| 8,399,047 B2 | 3/2013 | Lahann et al. |
| 8,463,418 B2 | 6/2013 | Liu et al. |
| 8,900,610 B2 | 12/2014 | Wellinghoff |
| 8,961,892 B2 | 2/2015 | Hutter et al. |
| 9,364,579 B2 | 6/2016 | Wellinghoff |
| 9,410,114 B2 | 8/2016 | Wilson et al. |
| 9,456,893 B2 | 10/2016 | Ling |
| 9,512,393 B2 | 12/2016 | Kasuto et al. |
| 9,593,308 B2 | 3/2017 | Har-Noy |
| 9,663,763 B2 | 5/2017 | Sentman |
| 10,052,372 B2 | 8/2018 | Wang et al. |
| 10,131,876 B2 | 11/2018 | Kaiser et al. |
| 10,179,151 B2 | 1/2019 | Ferber |
| 10,577,585 B2 | 3/2020 | Nguyen et al. |
| 2003/0119185 A1 | 6/2003 | Berenson et al. |
| 2004/0062809 A1 | 4/2004 | Honiger et al. |
| 2005/0038492 A1 | 2/2005 | Mason et al. |
| 2005/0238683 A1 | 10/2005 | Adhikari et al. |
| 2006/0121005 A1 | 6/2006 | Berenson et al. |
| 2007/0178586 A1 | 8/2007 | Yang et al. |
| 2008/0194010 A1 | 8/2008 | Liu |
| 2009/0041825 A1 | 2/2009 | Kotov et al. |
| 2010/0273667 A1 | 10/2010 | Kotov et al. |
| 2012/0009159 A1 | 1/2012 | Humayun et al. |
| 2012/0058560 A1 | 3/2012 | Derichs et al. |
| 2012/0208265 A1 | 8/2012 | Partsch et al. |
| 2013/0030548 A1 | 1/2013 | Ling |
| 2013/0084622 A1 | 4/2013 | Ram et al. |
| 2013/0344229 A1 | 12/2013 | Messersmith et al. |
| 2014/0199679 A1 | 7/2014 | Panoskaltsis et al. |
| 2015/0087057 A1 | 3/2015 | Zink et al. |
| 2015/0140333 A1 | 5/2015 | Niu |
| 2016/0200891 A1 | 7/2016 | Virgilio et al. |
| 2017/0028042 A1 | 2/2017 | Wang et al. |
| 2017/0051309 A1 | 2/2017 | Lesch et al. |
| 2017/0081638 A1 | 3/2017 | Ma |
| 2017/0312392 A1 | 11/2017 | Guilak et al. |
| 2017/0321178 A1 | 11/2017 | Ling et al. |
| 2018/0016533 A1 | 1/2018 | Tai et al. |
| 2018/0057784 A1 | 3/2018 | Wang et al. |
| 2018/0142200 A1 | 5/2018 | Mason et al. |
| 2019/0002815 A1 | 1/2019 | Wang et al. |
| 2019/0032011 A1 | 1/2019 | Better et al. |
| 2019/0169572 A1 | 6/2019 | Shi et al. |
| 2019/0211292 A1 | 7/2019 | Beauchesne et al. |
| 2019/0269768 A1 | 9/2019 | Wang et al. |
| 2019/0276846 A1 | 9/2019 | Lipponen et al. |
| 2019/0292517 A1 | 9/2019 | Cheung et al. |
| 2019/0309250 A1 | 10/2019 | Ling |
| 2020/0071670 A1 | 3/2020 | Shi et al. |
| 2020/0172864 A1 | 6/2020 | Chiang et al. |
| 2020/0181562 A1 | 6/2020 | Mcafee et al. |
| 2020/0190457 A1 | 6/2020 | Veraitch et al. |
| 2020/0208121 A1 | 7/2020 | Hewitt et al. |
| 2020/0248121 A1 | 8/2020 | Ferrie et al. |
| 2020/0248122 A1 | 8/2020 | Ferrie et al. |
| 2020/0248123 A1 | 8/2020 | Ferrie et al. |
| 2020/0248124 A1 | 8/2020 | Ferrie et al. |
| 2020/0255783 A1 | 8/2020 | Ferrie et al. |
| 2020/0255790 A1 | 8/2020 | Veraitch et al. |
| 2020/0255793 A1 | 8/2020 | Oconnor et al. |
| 2020/0283712 A1 | 9/2020 | Wang et al. |

FOREIGN PATENT DOCUMENTS

| | | |
|---|---|---|
| CN | 102428168 | 4/2012 |
| CN | 103328625 | 9/2013 |
| CN | 105126168 | 12/2015 |
| CN | 109689366 | 4/2019 |
| EP | 3351656 | 7/2018 |
| JP | 2005503156 | 2/2005 |
| JP | 2010517590 | 5/2020 |
| KR | 2013134080 | 12/2013 |
| WO | 1998/050522 | 11/1998 |
| WO | 2004087797 | 10/2004 |
| WO | 2008101001 | 8/2008 |
| WO | 2008140295 A1 | 11/2008 |
| WO | 2011072393 A1 | 6/2011 |
| WO | 2012168295 | 12/2012 |
| WO | 2014037862 A1 | 3/2014 |
| WO | 2015001321 A1 | 1/2015 |
| WO | 2015024133 | 2/2015 |
| WO | 2015086029 | 6/2015 |
| WO | 2017049066 A1 | 3/2017 |
| WO | 2017099712 A1 | 6/2017 |
| WO | 2017192717 | 11/2017 |
| WO | 2018005521 a1 | 1/2018 |
| WO | 2018013797 A1 | 1/2018 |
| WO | 2019194842 | 10/2019 |
| WO | 2020068840 | 4/2020 |

OTHER PUBLICATIONS

Office Action from related Chinese Application No. 201780036683.8, dated Sep. 27, 2021.

International Search Report and Written Opinion from related PCT Appln. No. PCT/US2021/070371, dated Jul. 23, 2021.

Sung-Wook Choi; et al., Neovascularization in Biodegradable Inverse Opal Scaffolds with Uniform and Precisely Controlled Pore Sizes, NIH Public Access—Adv Healthe Mater, Jan. 2013: 2(1), 18 pages.

Office Action dated Jan. 18, 2021, issued in Japanese Patent Application No. 2018-558237, 5 pages.

Office Action dated Feb. 16, 2021, issued in Indian Patent Application No. 201817044901, 5 pages.

Intent to Grant dated Feb. 2, 2021, issued in European Patent Application No. 17 793 249.8, 7 pages.

Notice of Allowance dated Jan. 13, 2021, issued in U.S. Appl. No. 15/585,812, 9 pages.

Corrected Notice of Allowability dated Mar. 26, 2021, issued in U.S. Appl. No. 15/585,812, 6 pages.

Preliminary Report on Patentability dated Apr. 1, 2021, issued in PCT Patent Application No. PCT/US2019/052713, 8 pages.

MAS.865 2018 "How to Make Something that Makes (almost) Anything";«http://fab.cba.mit.edu/classes/865.18/additive/multiphoton-polymerization/index.html» (accessed Mar. 30, 2020; 10 pgs).

Geng, Qiang, et al; "Ultrafast Multi-focus 3-D Nano-fabrication Based on Two-photon Polymerization"; «https://www.nature.com/articles/s41467-019-10249-2» (accessed Mar. 30, 2020; 7 pgs).

"Think Big. Print Nano. Your Partner for High-precision Additive Manufacturing" «https://www.nanoscribe.com/en/» (accessed Mar. 30, 2020; 7 pgs).

"Wide Range of Applications in Research, Prototyping and Production Processes Nanoscribe" «https://www.nanoscribe.com/en/applications» (accessed Mar. 30, 2020; 11 pgs).

Petrie Aronin, C., et al: "Comparative Effects of Scaffold Pore Size, Pore Volume, and Total Void Volume on Cranial Bone Healing Patterns Using Microsphere-based Scaffolds" Journal of Biomedical Materials Research Part A, Wiley InterScience Periodicals, Inc. published online Apr. 28, 2008 pp. 632-641.

Zeltinger, Ph D., J., et al: "Effect of Pore Size and Void Fraction on Cellular Adhesion, Proliferation, and Matrix Deposition"; Tissue

(56) References Cited

OTHER PUBLICATIONS

Engineering, vol. 7, No. 5, 2001, Mary Ann Liebert, Inc.; downloaded by EPO from «www.ieberpub.com» on Nov. 22, 2019 (pp. 557-572).
Extended European Search Report issued in corresponding European Patent Appln No. 1779329.8; dated Dec. 5, 2019 (16 pgs).
1st Written Opinion issued in corresponding Singapore Appln No. 11201809805W; dated Feb. 3, 2020 (6 pgs).
International Search Report; dated Jan. 23, 2020; issued in related PCT/US2019/52719 (11 pgs).
Preliminary Report on Patentability dated Nov. 15, 2018, issued in PCT Patent Application No. PCT/US2017/030833, 12 pages.
Office Action dated Jan. 23, 2019, issued in U.S. Appl. No. 15/585,812, 11 pages.
Office Action dated Oct. 29, 2019, issued in U.S. Appl. No. 15/585,812, 12 pages.
Office Action dated Aug. 7, 2020, issued in U.S. Appl. No. 15/945,000, 14 pages.
Office Action dated Sep. 28, 2020, issued in U.S. Appl. No. 15/585,812, 7 pages.
Käpylä et al., Direct laser writing and geometrical analysis of scaffolds with designed pore architecture for three-dimensional cell culturing, Journal of Micromechanics and Microengineering, 22, 2012, 13 pages.
Looby et al., Fixed bed porous glass sphere (porosphere) bioreactors for animal cells, Cytotechnology 1, Aug. 8, 1988, 339-346.
Ma et al., Biodegradable Polymer Scaffolds with Well0Defined Interconnected Spherical Pore Network, Tissue Engineering, vol. 7, No. 1, 2001, 17 pages.
Ma et al., Paraffin Spheres as Porogen to Fabricate Poly(L-Lactic Acid) Scaffolds with Improved Cytocompatibility for Cartilage Tissue Engineering, Department of Polymer Science and Engineering, Zhejiang University, Hangzhou China, Wiley Periodicals, Inc., 2003, 8 pages.
Malinauskas et al., 3D Microporous Scaffolds Manufactured via Combination of Fused Filament Fabrication and Direct Laser Writing Ablation, Micromachines, 5, 2014, 20 pages.
Intent to Grant dated Oct. 13, 2020, issued in European Patent Application No. 17793, 249.8, 7 pages.
Preliminary Report on Patentability dated Oct. 15, 2020, issued in PCT Patent Application No. PCT/US2018/031027, 7 pages.
Alves da Silva, M., et al, "Chondrogenic Differentiation of Human Bone Marrow Mesenchymal Stem Cells in Chitosan-Based Scaffolds Using a Flow-perfusion Bioreactor"; Journal of Tissue Engineering and Regenerative Medicine; 2011, 5(9), pp. 722-732.
Arifin, M., et al.: "Ultraviolet/Ozone (UV/O3) Treated Polystyrene (PS) Microcarriers for Animal Cell Culture"; Journal of Chemical Technology & Biotechnology 2016, 91(10): pp. 2607-2619.
Boland, E., et al; "In Vitro Cytotoxicity of a Low-shrinkage Polymerizable Liquid Crystal Resin Monomer"; Journal of Biomedical Materials Research Part B, Applied Biomaterials 2006, 79(1): pp. 1-6.
Caicedo-Carvajal, C.E.; 3D Perfusion Bioreactor: The Cumulative Advantages of 3D Scaffold Geometry and Perfusion for Scale-up Processes: 3D Biotek; Technology Center of NJ «http://www.3DBiotek.com» accessed Jun. 12, 2019.
Chen, G., et al "Scaffold Design for Tissue Engineering"; Macromolecular Bioscience, 2002, 2, pp. 67-77.
Cheung, A., et al; "Scaffolds That Mimic Antigen-Presenting Cells Enable Ex Vivo Expansion of Primary T Cells"; Nature Biotechnology vol. 36, No. 2, Feb. 2018.
Choi, S., et al; "Alzheimer's Disease and Stem Cell Therapy"; Experimental Neurobiology 2014, vol. 23(1), pp. 45-52.
Dynabeads™ Human T-Activator CD3/CD28 for T Cell Expansion and Activation «https://www.thermofisher.com/order/catalog/product/11161D» accessed Aug. 30, 2018.
Elkasabi, Y., et al; "Towards Multipotent Coatings: Chemical Vapor Deposition and Biofunctionalization of Carbonyl-Substituted Copolymers"; Macromolecular Rapid Communications 2008, 29(11): pp. 855-870.

Fenge, C., et al; Sartorius Stedim Biotech; Large-Scale Perfusion and Concentrated Fed-Batch Operation of Biostat® STR Single-Use Bioreactor.
Frith, J., et al; "Dynamic Three-Dimensional Culture Methods Enhance Mesenchymal Stem Cell Properties and Increase Therapeutic Potential"; Tissue Engineering Part C, Methods 2010, vol. 16(4): 735-749.
Gardel, L., et al; "A Novel Bidirectional Continuous Perfusion Bioreactor for the Culture of Large-sized Bone Tissue-engineered Constructs"; Society for Biomaterials, Journal of Biomedical Materials Research B: Applied Biomaterials; Nov. 2013, vol. 10 1B, Issue 8, pp. 1377-1386.
General Electric Wave Bioreactor Systems, Cell Culture Procedures «www.gelifesciences.com/wave» accessed Apr. 18, 2017.
Glavaski-Joksimovic, A., et al; "Mesenchymal Stem Cells and Neuroregeneration in Parkinson's Disease", Experimental Neurology 2013, vol. 247, pp. 25-38.
Gordon, G., et al; "The Chemistry of Chlorine Dioxide"; Progress in Inorganic Chemistry 1972, vol. 15: pp. 201-286.
Han, Y., et al; "High-Performance Nano-Photoinitiators with Improved Safety for 3D Printing"; ACS Applied Materials and Interfaces 2017, 9(38): pp. 32418-32423.
Higuera, G., et al; "The Physics of Tissue Formation with Mesenchymal Stem Cells"; Trends in Biotechnology, Nov. 2012, vol. 30, No. 11; pp. 583-590.
Kaiser, A., et al; "Towards a Commercial Process For the Manufacture of Genetically Modified T Cells For Therapy"; https://www.nature.com/articles accessed Mar. 26, 2018.
Kim, J., et al; "Bioreactor Strategy in Bone Tissue Engineering: Pre-Culture and Osteogenic Differentiation Under Two Flow Configurations"; Tissue Engineering: Part A 2012, vol. 18, Nos. 21-22: pp. 2354-2364.
Ko, H, et al; "One Step Immobilization of Peptides and Proteins by Using Modified Parylene with Formyl Groups"; Biosensors and Bioelectronics 2011, 30(1): pp. 56-60.
Kumar, A, et al; "Human Mesenchymal Stem Cells Expansion on Three-Dimensional (3D) Printed Poly-Styrene (PS) Scaffolds in a Perfusion Bioreactor"; Science Direct 2017, vol. 65, pp. 115-120.
Kumar, A., et al "Large Scale Industrialized Cell Expansion Producing the Critical Raw Material for Biofabrication Processes"; Biofabrication 7(4): 044103 (2015).
Kwon, T., et al; "Microfluidic Cell Retention Device for Perfusion of Mammalian Suspension Culture"; Scientific Reports 7:6703, 2017; «https://www.nature.com/articles/s41598-017-06949-8» accessed Mar. 26, 2018.
Lechanteur, C., et al "Large-Scale Clinical Expansion of Mesenchymal Stem Cells in the GMP-Compliant, Closed Automated Quantum® Cell Expansion System: Comparison with Expansion in Traditional T-Flasks"; Journal of Stem Cell Research & Therapy 2014, 04(08).
Ligon, S. et al; "Polymers for 3D Printing and Customized Additive Manufacturing", Chemical Reviews 2017, 117(15): pp. 10212-10290.
Mirro, R., "An Update on the Advantages of Fibra-Cel® Disks for Cell Culture"; eppendorf, Application Note No. 313, Jul. 2011.
Papadimitropoulos, A., et al; "Expansion of Human Mesenchymal Stromal Cells From Fresh Bone Marrow in a 3D Scaffold-Based System Under Direct Perfusion"; PLOS ONE, Jul. 2014, vol. 9, Issue 7.
Portner, R., et al; "Fixed Bed Reactors for the Cultivation of Mammalian Cells: Design, Performance and Scale-Up"; The Open Biotechnology Journal, 2007, 1, 41-46.
Provin, C., et al "A Method for the Design of 3D Scaffolds for High-Density Cell Attachment and Determination of Optimum Perfusion Culture Conditions"; Journal of Biomechanics 41 (2008) 1436-1449.
Sailon, A., et al "A Novel Flow-Perfusion Bioreactor Supports 3D Dynamic Cell Culture"; Journal of Biomedicine and Biotechnology, vol. 2009, Article ID 873816.
Schop, D., et al "Expansion of Mesenchymal Stem Cells Using a Microcarrier-based Cultivation System: Growth and Metabolism"; Journal of Tissue Engineering and Regeneration Medicine; 2008, 2L 126-135.

(56) References Cited

OTHER PUBLICATIONS

Sobral, JM et al "Three-Dimensional Plotted Scaffolds With Controlled Pore Size Gradients: Effect of Scaffold Geometry On Mechanical Performance and Cell Seeding Efficiency" Acta Biomaterialia, vol. 7, Issue 3, Mar. 2011, pp. 1009-1018 cited as Y PCT/US17/30833 in the ISR & WO, date of mailing Aug. 2, 2017 (10 pgs).
Specialty Coating Systems Parylene Properties «https://scscoatings.com/docs/brochures/parylene_properties.pdf» accessed Aug. 30, 2018.
Tan, C., et al; "Surface Engineering and Patterning Using Parylene for Biological Applications"; Materials 2010, 3(3): pp. 1803-1832.
Van Den Driesche, S., et al; "3D Printing Solutions for Microfluidic Chip-to-World Connections"; Micromachines 2018, 9: 71 (12 pgs).
Vitale, A., et al; "Frontal Conversion and Uniformity in 3D Printing by Photopolymerisation",. Materials 2016, 9(760), 13 pgs.
Weber, C. et al (2010) Production Process for Stem Cell Based Therapeutic Implants: Expanson of the Production Cell Line and Cultivation of Encapsulated Cells. Retrieved from http://krex.ksu.edu.
Wellinghoff, S., et al; Advanced Dental Restorative Composites Utilizing Low Polymerization Shrinkage Liquid Crystalline Monomers In: Physical Chemistry 2006. Belgrade, Serbia; 2006, (8 pgs).
Wen, Z., et al "Repair Mechanisms of Bone Marrow Mesenchymal Stem Cells in Myocardial Infarction". Journal of Cellular and Molecular Medicine 2011, vol. 15, No. 5, pp. 1032-1043.
Whitford, W., et al "Single-Use, Continuous Processing of Primary Stem Cells"; BioProcess International, Cell Therapy Processing; Mar. 2014, 12(3):26-33.
Wu, H., et al; "Mesenchymal Stem Cell-based Therapy for Type 1 Diabetes"; Discovery Medicine 2014, vol. 17(93); pp. 139-143.
Yamada, S., et al; "Multi-Sized Sphere Packing"; «http://www2.latech.edu/-jkanno/packing.pdf»; dated Jul. 4, 2009; pp. 7-8 cl20; cited as Y in the ISR & WO, date of mailing Aug. 2, 2017; of related application No. PCT/US17/30833.
Yang, S., et al: "Mussel-Inspired Encapsulation and Functionalization of Individual Yeast Cells"; Journal of the American Chemical Society, 133, 2795-2797, 2011.
Yeatts, A., et al; "Bioreactors to Influence Stem Cell Fate: Augmentation of Mesenchymal Stem Cell Signaling Pathways Via Dynamic Culture Systems"; Biochimica et Biophysica Acta 2013, 1830 (2); pp. 2470-2480.
Yourek, G, et al; "Shear Stress Induces Osteogenic Differentiation of Human Mesenchymal Stem Cells"; Regenerative Medicine 2010, vol. 5, No. 5; pp. 713-724.
Zhang, J., et al; "Fabrication of Three Dimensional Polymeric Scaffolds With Spherical Pores"; J. Mater Sci 41 (2006) pp. 1725-1731 cited as A in PCT/US18/31027 ISR/WO dated Jul. 23, 2018.
ISR & WO issued in PCT/US2017/30833, dated Aug. 2, 2017 (14 pgs).
ISR & W/O dated Jul. 23, 2018 (issued in related PCT/US18/31027 (9 pgs).
Choi, et al "Three-Dimensional Scaffolds for Tissue Engineering: The Importance of Uniformity in Pore Size and Structure" American Chemical Society, Langmuir Article published on Web Nov. 23, 2010, 26(24), pp. 19001-19006.
Lee, et al: "Three-Dimensional Cell Culture Matrices: State of the Art"; Tissue Engineering: Part B, vol. 14, No. 1, 2008, pp. 61-86.
First Office Action from related Australian Appln. No. 2017261267, dated Jan. 17, 2022.
Office Action from related Japanese Appln. No. 2020-554460, dated Apr. 11, 2022. English translation attached.
Office Action from related Singaporean Appln. No. 11202009803T, dated May 24, 2022.
Supplemental Partial European Search Report from related Application No. 19866434.4, dated Jun. 9, 2022.

THREE-DIMENSIONAL BIOREACTORS

CROSS-REFERENCE TO RELATED APPLICATIONS

The present application claims the benefit of the filing date of U.S. Provisional Application 62/735,531 filed on Sep. 24, 2018, the teachings of which are incorporated by reference.

FIELD OF THE INVENTION

The present invention relates to the design, fabrication and applications of three-dimensional (3D) bioreactors for cell expansion and cell secreted substance production. The invention includes methods of reducing or preventing of cytotoxic leaching of 3D bioreactors or other components where fabricated via in situ photo-polymerization based 3D printing techniques. The methods include the combination of 3D printing material with relatively high photo-polymerization efficiency, post-printing UV curing, post-printing heat/vacuum extraction, and post-printing coatings with substituted or unsubstituted poly(p-xylene) type material.

BACKGROUND

Cancer immunotherapy, representing the most recent phase of biotechnology revolution in medicine, is the use of a patient's own immune system to treat cancer. A recent successful case is the chimeric antigen receptor (CAR) T-cell based cancer treatment. A typical CAR T-cell therapy process is one in which T lymphocytes are collected from a patient's own blood are genetically engineered to produce a special receptor CAR on their surface so that the T cells are able to recognize and attack cancer cells. The engineered CAR T cells are grown in the laboratory and expanded to billions of numbers and then injected back to the patient to kill cancer cells.

With the successful of CAR T-cell therapy, the next question is how to make it safer and cost-efficient. The current T-cell engineering process is still generally based on the use of magnetic beads to incubate together with T-cells. The magnetic beads are coated with CD3 and CD28 on their surface to act as the antigens to activate the T-cells so they can proliferate. The micro-beads suspended in cell culture medium with T-cells provide a relatively large surface area for T-cells to contact and temporarily bind to CD3 and CD28 and then activate. After T-cells are grown to a certain density, the T-cells and magnetic beads are moved into a relatively large bioreactor such as the GE's WAVE bioreactor to continue the process of stimulation and expansion. The process is repeated multiple times to grow relatively large numbers of T-cells. At harvesting, the T cells have to be separated from the beads using a magnetic separator. Accordingly, the current T-cell expansion process generally relies upon magnetic beads, multi-stage processing, and manual interactions, which is not cost-effective. In addition, it is an open system, which can easily introduce contaminations and make it relatively more expensive to meet good manufacturing process (GMP) requirements.

Accordingly, a need remains for methods and devices to improve cellular expansion, and in particular T-cell expansion, by offering improved bioreactor designs, cost-effective fabrication techniques, and improved bioreactor operating capability in order to achieve clinical application dose requirements.

Another pressing need is a device to provide efficient expansion of adherent cells such as the stem cells. With the recent development of stem cell technology and regenerative medicine, the number of stem cell-based therapies has increased significantly. Stem cells have the potential to cure many human diseases because they are not yet specialized, and can differentiate into many types of cells for tissue repair and regeneration. Large-scale cell expansion is one of the bottlenecks in stem cell based therapy and tissue regeneration. Typically, there are $10^9$ cells in one gram of tissue. However, the number of replicating cells harvested from a donor is extremely low (~$10^5$ cells), which necessitates approximately 10,000-fold cell expansion for clinical applications. The conventional 2D planar T-flask method for cell culture is relatively difficult to scale-up. The manual process using the T-flask is labor-intensive, susceptible to contamination, and requires high cost to meet cGMP cell manufacturing standards. Commercially available 3D cell expansion devices based on stacked plates, microcarriers, and hollow fibers also have several limitations, including: limited scalability, lack of critical process control, high shear stress, large nutrition gradient, and complex downstream processing. In the present disclosure, we describe the design, fabrication, and applications of a device as a 3D bioreactor for cell expansion and production of cell secreted substances.

SUMMARY

A 3D bioreactor for growth of cells comprising a plurality of voids having a surface area for cell expansion, said plurality of voids having a diameter D, a plurality of pore openings between said voids having a diameter d, such that D>d and wherein: (a) 90% or more of said voids have a selected void volume (V) that does not vary by more than +/−10.0%; and (b) 90% or more of said pore openings between said voids have a value of d that does not vary by more than +/−10.0%; and coating said bioreactor with substituted or unsubstituted poly(p-xylylene).

A 3D bioreactor for growth of cells comprising a plurality of voids having a surface area for cell expansion, said plurality of voids having a diameter D, a plurality of pore openings between said voids having a diameter d, such that D>d and wherein: (a) 90% or more of said voids have a selected void volume (V) that does not vary by more than +/−10.0%; and (b) 90% or more of said pore openings between said voids have a value of d that does not vary by more than +/−10.0%;

wherein said bioreactor comprises the polymerization product of the following monomer:

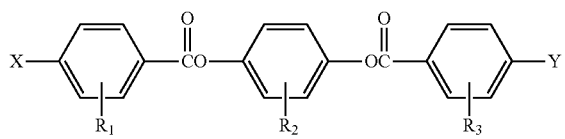

wherein X and Y comprise polymerizable groups that are polymerized by free-radical polymerization, $R_2$ is a bulky organic group having a bulk greater than $R_1$ and $R_3$, wherein $R_2$ is adapted to provide sufficient steric hindrance to achieve a nematic state at room temperature.

BRIEF DESCRIPTION OF THE DRAWINGS

FIG. 5c indicates a scale of shear stress in unit Pa.

DETAILED DESCRIPTION OF PREFERRED EMBODIMENTS

The present disclosure relates to a perfusion-based scalable bioreactor design and with corresponding operating capability to achieve T-cell expansion for immunotherapy purposes or stem cell expansion for regenerative medicine. The activation and expansion of T-cells or stem cells from a patient, after for example, gene-modification, provides a therapeutic T-cell or stem cell product that can be infused back to the patient and uses patient's own immune system in a manner that selectively targets and kills the patient's tumor cells or uses the patient's own regenerative cells for curing aging related diseases.

Reference to a bioreactor herein refers to the disclosed 3D reactor in which biological and/or biochemical processes can be implemented under selected environmental and operating conditions. This includes control of one or more of the following: geometry/size of the voids, interconnected pore size between the voids and total number of voids included (determining the overall dimension of the bioreactor). In addition, one may selective control surface coatings, flow characteristics through the voids within the bioreactor, pH, temperature, pressure, oxygen, nutrient supply, and/or waste removal. Clinical dosage requirements are reference to the ability to provide a dose of $10^9$ cells or greater.

Figure 1:
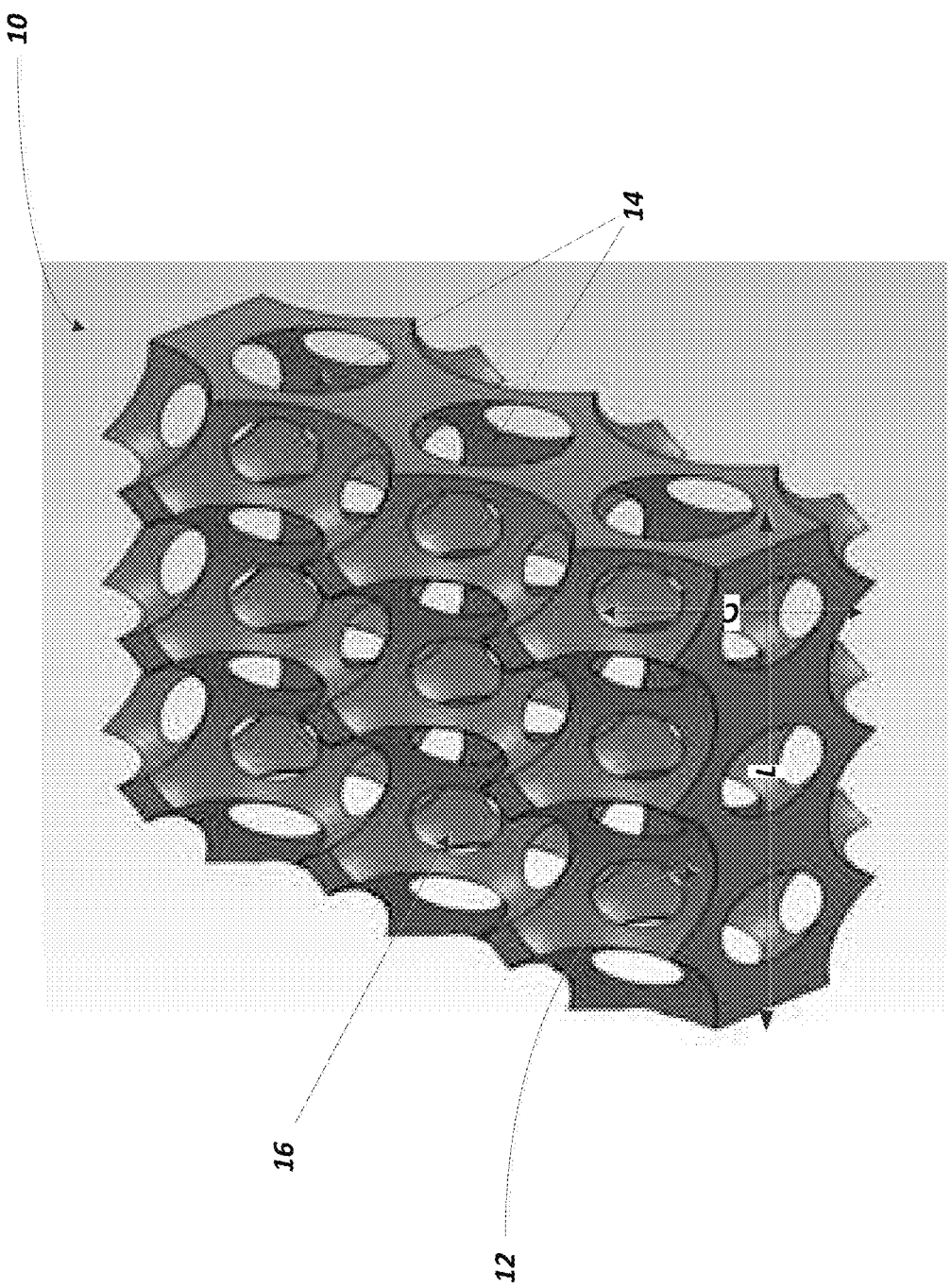
FIG. 1 illustrates a section view of the 3D bioreactor fixed-bed.

The 3D bioreactor's preferred fixed-bed 10 is generally illustrated in cut-away view in FIG. 1, which shows an example of a preferred packed and spherical void structure and their interconnected pores between the spherical voids. More specifically, the bioreactor includes a continuous interconnected 3D surface area 12 that provides for the ability for the cells to bind in the present of antibodies and also defines within the bioreactor a plurality of interconnected non-random voids 14 which as illustrated are preferably of spherical shape with internal concave surfaces to maximize the surface to volume ratio. A void is understood as an open space of some defined volume. By reference to non-random it should be understood that one can now identify a targeted or selected number of voids in the 3D bioreactor that results in an actual repeating void size and/or geometry of a desired tolerance.

By reference to a continuous surface, it is understood that the expanding cells can readily migrate from one surface area location into another within the 3D bioreactor, and the surface does not include any random interruptions, such as random breaks in the surface or random gaps of 0.1 mm or more. Preferably, 50% or more of the surface area within the 3D bioreactor for cell expansion is a continuous surface, more preferably, 60% or more, 70% or more, 80% or more, 90% or more, 95% or more or 99% or more of the surface area within the 3D bioreactor is continuous.

In addition, the bioreactor fixed-bed 10 includes non-random interconnecting pore openings 16 as between the voids. Again, reference to non-random should be understood that one can now identify a targeted or selected number of pores for the voids, of a selected pore diameter, that results in an actual number of pores having pore diameters of a desired tolerance. The bioreactor as illustrated in cut-away view also ultimately defines a layer of non-random voids (see arrow "L") and it may be appreciated that the multiple layers of the bioreactor may then allow for identification of a plurality of such non-random voids within a column (see arrow "C").

The bioreactor may be made of biocompatible or bio-inert polymeric materials such as polystyrene, polycarbonate, acrylonitrile-butadiene-styrene (ABS), polylactic acid (PLA), polycaprolactone (PCL) used in FDM (fused deposition modeling) 3D printing technology. Reference to biocompatible or bio-inert should be understood as a material that is non-toxic to the culturing cells. In addition, the polymeric materials for the 3D bioreactor are preferably selected from those polymers that at not susceptible to hydrolysis during cell cultivation, such that the amount of hydrolysis does not exceed 5.0% by weight of the polymeric material present, more preferably it does not exceed 2.5% by weight, and most preferably does not exceed 1.0% by weight. The bioreactor may also be made of biocompatible materials (e.g., poly(methyl methacrylate) or PMMA, etc.) used in SLA (stereolithography) and DLP (digital light processing) 3D printing technologies.

The bioreactor herein may also be preferably made from biocompatible, liquid crystalline, photopolymerizable monomers described in U.S. Pat. Nos. 7,041,234; 7,094,360; 7,098,359; 7,108,801; 7,147,800; and 7,238,831, which are hereby incorporated by reference. Accordingly, the monomers herein that may also be employed to form the 3D bioreactor herein may be described as having the following structure:

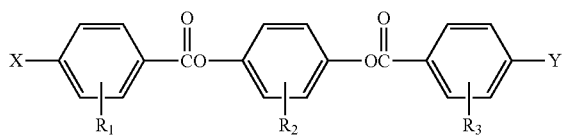

In the above, X and Y comprise polymerizable groups, which may be polymerized by free radical polymerization or by nucleophilic addition, including but not necessarily limited to Michael addition. Examples include unsaturated carbon-carbon bonds and epoxy end groups. Preferred end groups therefore may include substituted and unsubstituted alkenyl ester groups comprising an unsaturated carbon-carbon bond (e.g. —OC(O)—CH=CH$_2$ or —OC(O)—C(CH$_3$)=CH$_2$). $R_2$ is a bulky organic group having a bulk greater than $R_1$ and $R_3$, wherein $R_2$ is adapted to provide sufficient steric hindrance to achieve a nematic state at room temperature while suppressing crystallinity of the liquid crystalline monomer. Accordingly, $R_1$ and $R_3$ are selected from groups less bulky than $R_2$. Suitable $R_2$ groups include but are not necessarily limited to t-butyl groups, isopropyl groups, phenyl groups, and secondary butyl groups. Particularly preferred $R_2$ groups include t-butyl groups. $R_1$ and $R_3$ are less bulky than $R_2$ and preferably selected from hydrogen atoms and methyl groups. Blends of different monomers of this type may also be used to minimize starting monomer viscosity and polymerization shrinkage and to maximize polymerization conversion to produce minimal residual monomer and to optimize final polymer mechanical properties. It is contemplated that starting zero shear monomer viscosity would be in the range of 5 Poise to 300 Poise at temperatures of 25° C. to 70° C., polymerization conversion would be in the range of at least 75% and higher, more preferably greater than or equal to at least 90%. Also, the as formed polymer preferably has the following mechanical strength characteristics: (1) flexural modulus at room temperature of at least 1500 MPa, and in the range of 1500 MPa to 2500 MPa; (2) flexural strength at room temperature of at least 70 MPa and more preferably in the range of 70 MPa to 100 MPa. Moreover, the polymerization shrinkage at less than or equal to 5%, more preferably in the range of 0.5% to 4.0%. In addition the liquid crystalline monomer blends of the structure illustrated above may be mixed with photoinitiator and thermal initiator systems and viscosity modifiers while still maintaining the liquid crystalline state.

It is preferable that the material used to fabricate the bioreactor is not degradable in aqueous medium and can provide a mechanically stable structure to tolerate aqueous medium flow during cell expansion. It is preferable that the material and manufacturing process can result a solid and smooth interconnected surface area for monolayer cell expansion. By reference to a solid surface, it should be understood that the surface is such that it will reduce or prevent penetration or embedding by the culturing cells, which typically have a diameter of about 20 microns to 100 microns. Preferably, the 3D bioreactor herein is one that has a surface that has a surface roughness value (Ra), which is reference to the arithmetic average of the absolute values of the profile height deviations from the mean line, recorded within an evaluation length. Accordingly, it is contemplated herein that Ra of the 3D bioreactor surface will have a value of less than or equal to 20 µm, more preferably, less than or equal to 5 µm.

The 3D bioreactor herein is also preferably one that is formed from material that indicates a Shore D Hardness of at least 10, or in the range of 10-95, and more preferably in the range of 45-95. In such regard, it is also worth noting that the 3D bioreactor herein is one that does not make use of a hydrogel type structure, which may be understood as a hydrophilic type polymeric structure, that includes some amount of crosslinking, and which absorbs significant amounts of water (e.g., 10-40% by weight). It is also worth noting that the 3D bioreactor herein is one that preferably does not make use of collagen, alginate, fibrin and other polymers that cells can easily digest and undergo remodeling.

Furthermore, the 3D bioreactor herein is preferably one that is made from materials that have a Tensile Modulus of at least 0.01 GPa. More preferably, the Tensile Modulus has a value that is in the range of 0.01 GPa to 20.0 GPa, at 0.01 GPa increments. Even more preferably, the Tensile Modulus for the material for the 3D bioreactor is in the range of 0.01 GPa to 10.0 GPa or 1.0 GPa to 10 GPa. For example, with respect to the earlier referenced polymeric materials suitable for manufacture of the 3D bioreactor herein, polystyrene indicates a Tensile Modulus of about 3.0 GPa, polycarbonate at about 2.6 GPa, ABS at about 2.3 GPa, PLA at about 3.5 GPa, PCL at about 1.2 GPa, and PMMA at about 3.0 GPa.

The 3D bioreactor design herein with such preferred regular geometric characteristics and continuous surface area is preferably fabricated by additive manufacturing technologies, such as FDM, selective laser sintering (SLS), stereolithography (SLA), digital light processing (DLP) 3D printing technologies, etc., according to computer generated designs made available by, e.g., a SolidWorks™ computer-aided design (CAD) program.

By way of preferred example, the process utilizing Solid-Works™ to create the 3D bioreactor design is described below. A computer model for the bioreactor negative is initially created. More specifically, what may therefore be described as a 3D bioreactor negative was created, e.g., using packed 6.0 mm diameter spheres that overlap to create 1.0 mm diameter connecting pores between spheres. Of course, other possible dimensions are contemplated within the broad context of this disclosure.

The spheres are preferably organized in a hexagonal close packed (HCP) lattice to create an efficiently (or tightly) packed geometry that results in each sphere surrounded by 12 neighborhood spheres. A unit cell of this exemplary geometry is shown in FIG. 1a. More specifically, in FIG. 1a there is a unit cell of the HCP lattice where the top three spheres are displayed as translucent to show the 6 radial overlapping areas between the neighborhood spheres. The pores are formed at these overlapping areas. Preferably, the maximum number of pores is 12 to optimize packing. The minimum pore number is 2 in order to allow medium perfusion through the voids of the 3D bioreactor. Accordingly, at least 90.0% to 100% of the voids present in the 3D bioreactor have at least 2 pore openings per void. More preferably, at least 90.0% to 100% of the voids in the 3D bioreactor have 8-12 pore openings per void. In one particularly preferred embodiment, at least 90.0% to 100% of the voids in the 3D bioreactor have 12 pore openings per void.

Figure 1B:
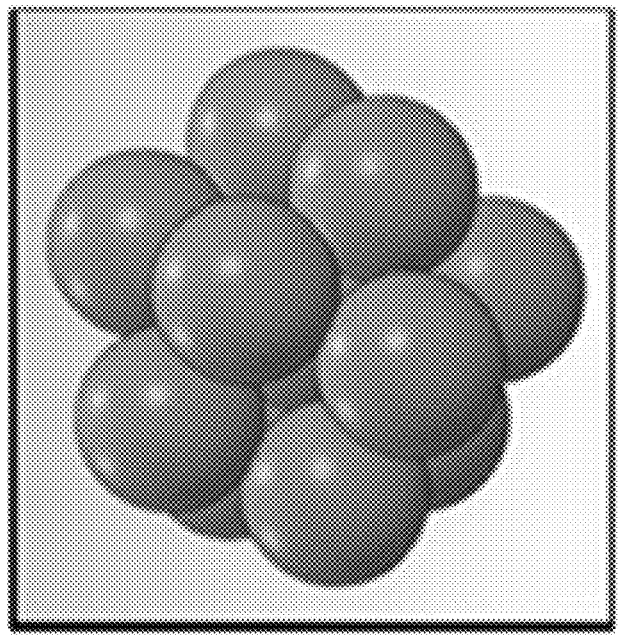
FIG. 1b illustrates a unit negative model with each sphere surrounded by 12 identical neighborhood spheres.
Figure 1A:
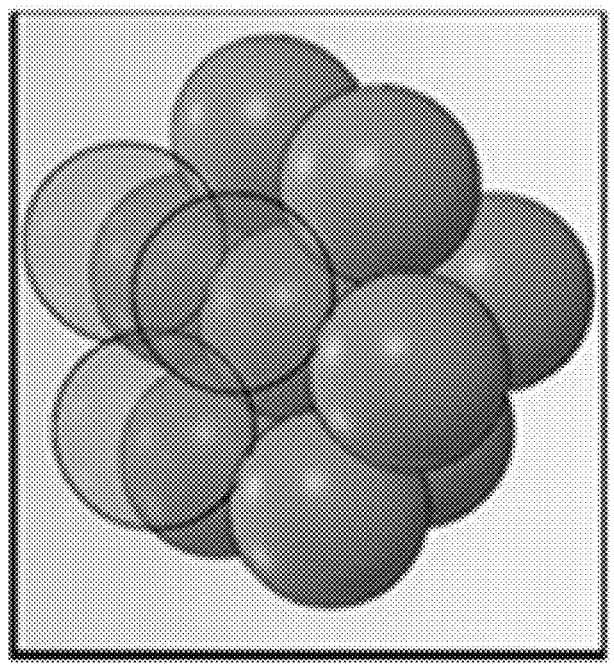
FIG. 1a illustrates a unit negative model of the bioreactor that shows the overlapping of the neighborhood spheres.
Figure 1D:
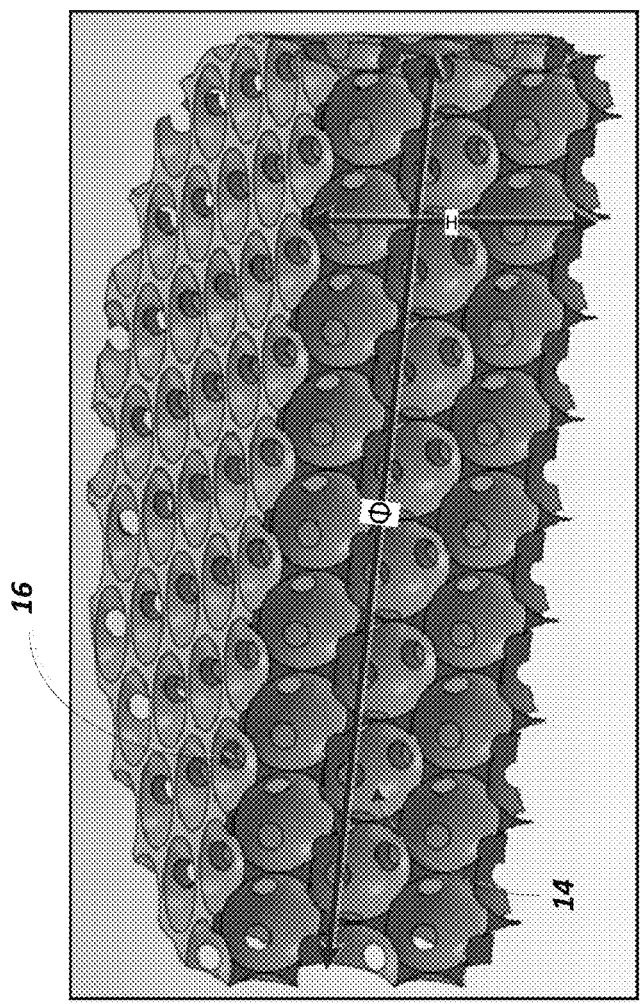
FIG. 1d illustrates a 3D bioreactor fixed-bed geometry in cross-sectional view.
Figure 1C:
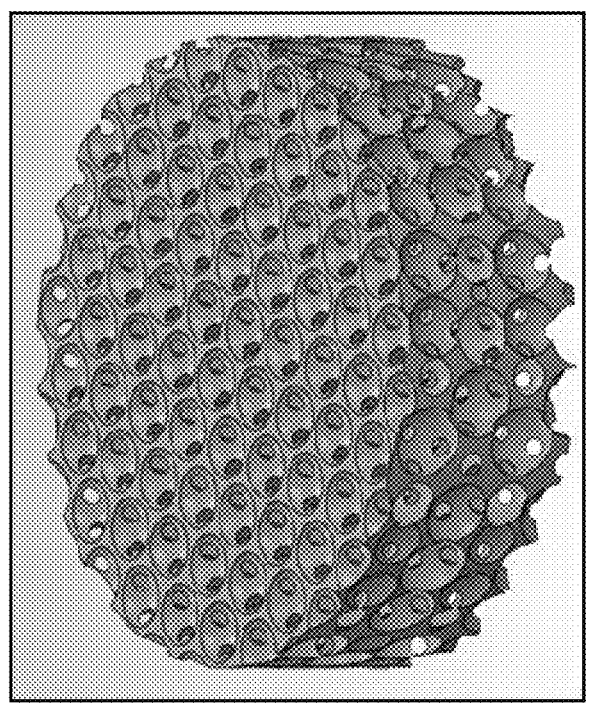
FIG. 1c illustrates a 3D bioreactor fixed-bed geometry showing an interconnected void system.

In FIG. 1b, all spheres of the unit are illustrated. The bioreactor geometry is then preferably created by reversing the negative model to create the positive model comprising an interconnected spherical void system shown in FIG. 1c. Moreover, in FIG. 1d one can see the 3D bioreactor again in cross-sectional view providing another illustration of the interconnected voids shown in cut-away view at 14 with regular geometric characteristics (substantially the same control of void volume as described above) and the corresponding interconnected pore openings 16.

Figure 1E:
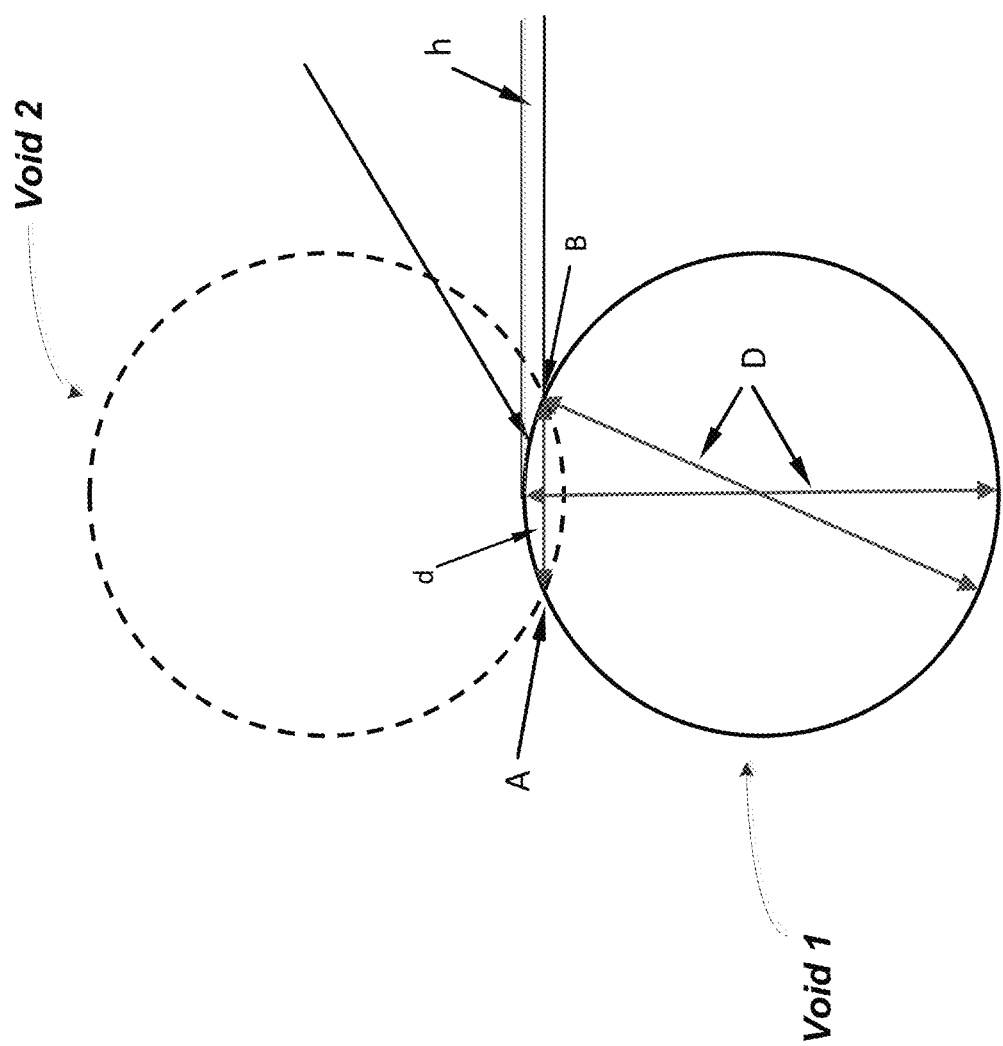
FIG. 1e illustrates in 2D view the identified spherical voids of a 3D bioreactor, and their overlapping areas to form interconnected pores between the spherical voids.

In the preferred regular geometric 3D bioreactor described above, one can identify a relationship as between the void diameter and interconnected pore diameter. Attention is directed to FIG. 1e. For this preferred geometry, Spherical Void 1 is represented by a solid circle, diameter is D (indicated by the arrows). Diameter "D" may therefore be understood as the longest distance between any two points on the internal void surface. Spherical Void 2 is represented by a dash circle and would also have diameter D (not shown). Spherical Void 2 is one of the 12 of neighborhood voids of Spherical Void 1. Due to the overlap between the neighborhood voids, it forms interconnected pores between the spherical voids, with the diameter of "d" as also indicated by the generally horizontal arrow. Diameter "d" may therefore be understood as the longest distance between any two points at the pore opening. The total 3D spherical surface area of the void is $SA_{void}=4\times\pi\times(D/2)^2$. The surface area between A and B, called $S_{cap}=\pi\times D\times h$, where $$h = \frac{D - \sqrt{D^2 - d^2}}{2}.$$

The useful void surface for a given void in the 3D bioreactor would be $SA_u=SA_{void}-[12\times S_{cap}]$.

The smaller the void diameter D, the larger the number of voids can be packed into a set 3D space (volume), and therefore results larger overall cell binding surface. However, to minimize or prevent cell aggregation to block the perfusion, the minimal diameter of the pores is preferred d=0.2 mm for this geometry. The diameter of the pores d may fall in the range of 0.2 mm to 10 mm and more preferably 0.2 mm to 2.0 mm. Most preferably, d≥0.5 mm and falls in in the range of 0.5 mm to 2.0 mm.

If D=0.40 mm or less, the computed $SA_u$ is less than 0 when d=0.2 mm, which leads to an impossible structure therefore, D has to be >0.4 mm for this 3D bioreactor geometry. However, D can have a value between 0.4 mm to 100.0 mm, more preferably, 0.4 mm to 50.0 mm, and also in the range of 0.4 mm to 25.0 mm. One particularly preferred value of D falls in the range of 2.0 mm to 10.0 mm. Spherical voids with a relatively large value of D may reduce the objective of increasing cell culture surface area as much as possible within a same bioreactor volume. Accordingly, for the preferred geometry illustrated in FIG. 1e, D>0.4 mm (the diameter of the void) and d>0.20 mm (the diameter of the pores). It is also worth noting that with respect to any selected value of diameter D for the voids in the range of 0.4 mm to 100.0, and any selected value of diameter d for the pores in the range of 0.2 mm to 10.0 mm, the value of D is such that it is greater than the value of d (D>d).

It can now be appreciated that the 3D bioreactor herein can be characterized with respect to its non-random characteristics. Preferably, all of the voids within the 3D bioreactor are such that they have substantially the same volume to achieve the most efficient 3D space packing and offer the largest corresponding continuous surface area. With respect to the total number of interconnected voids present in any given 3D bioreactor, preferably, 90.0% or more of such voids, or even 95.0% or more of such voids, or even 99.0% to 100% of such voids have a void volume (V) whose tolerance is such that it does not vary by more than +/−10.0%, or +/−5.0%, or +/−2.5% or +/−1.0%, or +/−0.5% or +/−0.1%. It should be noted that while the voids in FIG. 1 are shown as generally spherical, other voids geometries are contemplated. The diameter of voids are chosen to minimize or avoid cell aggregation and to provide maximum useful surface area for cell culturing.

Another non-random characteristic of the 3D bioreactor herein are the pore openings between the voids, having a diameter d (see again FIG. 1e). Similar to the above, 90.0% or more of the pore openings, or even 95.0% or more of the pore openings, or even 99.0% to 100% of the pore openings between the voids, indicate a value of d whose tolerance does not vary more than +/−10.%, or +/−5.0%, or +/−2.5% or +/−1.0%, or +/−0.5% or +/−0.1%.

It can therefore now by appreciated that the 3D bioreactor herein for growth of non-adherent cells comprises a surface area for cell binding, a plurality of voids having a diameter D (the longest distance between any two points on the internal void surface), a plurality of pore openings between said voids having a diameter d (the longest distance between any two points at the pore opening), where D>d. In addition, 90% or more of the voids have a void volume (V) that does not vary by more than +/−10.0%, and 90% or more of the pore openings have a value of d that does not vary by more than +/−10.0%.

In addition, the 3D bioreactor herein for expansion of non-adherent cells like T-cells can include a first plurality of voids having a diameter $D_1$, a plurality of pore openings between said first plurality of voids having a diameter $d_1$, wherein $D_1>d_1$, where 90% or more of the first plurality of voids have a void volume ($V_1$) with a tolerance that does not vary by more than +/−10.0%. Such 3D bioreactor may also have a second plurality of voids having a diameter $D_2$, a plurality of pore openings between said second plurality of voids having a diameter $d_2$ wherein $D_2>d_2$, wherein 90% of the second plurality of voids have a void volume ($V_2$) with a tolerance that does not vary by more than +/−10.0%. The values of $V_1$ and $V_2$ are different and outside of their tolerance variations. Stated another way, the value of $V_1$, including its tolerance of +/−10.0% and the value of $V_2$, including its tolerance of +/−10.0%, are different, or [$V_1$+/−10.0%]≠[$V_2$+/−10.0%].

The radius of curvature (Rc) of the surface within the voids is therefore preferably 1/0.5 (D), or 1/0.2 mm=5 mm$^{-1}$ or lower. Preferably, Rc may have a value of 0.2 mm$^{-1}$ to 1.0 mm$^{-1}$, which corresponds to a value of D of 10.0 mm to 2.0 mm. A high curvature (large Rc) surface provides a significantly different environment than the typical monolayer 2D culture, which may also induce cell phenotype changes.

Cells are preferably bound on the interconnected spherical void surfaces of the 3D bioreactor. Such 3D structure is preferably scalable and is able to provide a relatively high surface to volume ratio for relatively large cell expansion with a relatively small footprint cell expansion bioreactor. The surface area-to-volume ratio is also preferably determined by the diameter of the spherical voids. The smaller is the diameter, the higher is the surface area-to-volume ratio. Preferably, the voids provide a relatively "flat" surface (i.e., low radius of curvature≤1.0 mm$^{-1}$) for cells having a size of 5 µm to 100 µm and also to reduce or avoid cell aggregation. In addition, as alluded to above, cell aggregation is also reduced or avoided by controlling the diameter d of the interconnected pores, which diameter is preferably at least 500 µm, but as noted, any size greater than 200 µm.

Figure 2:
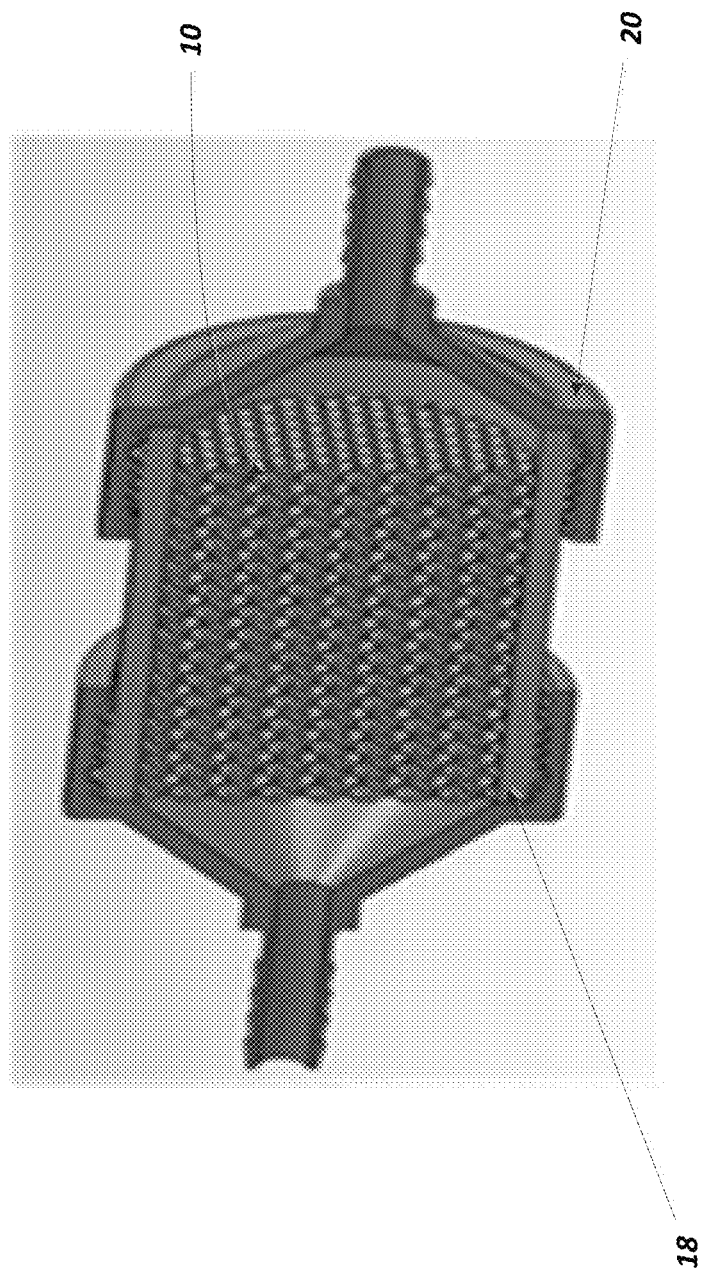
FIG. 2 illustrates a 3D bioreactor fixed-bed positioned in a housing with inlet and outlet for fluid perfusion.
Figure 3:
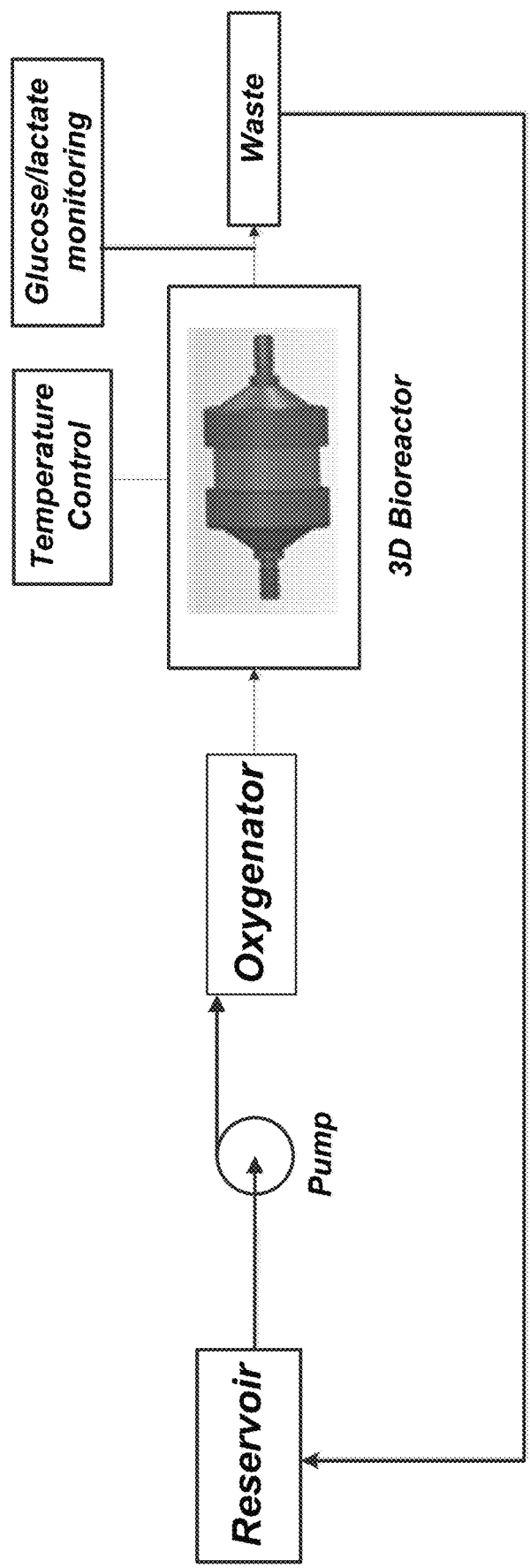
FIG. 3 illustrates a typical 3D bioreactor perfusion system.

The bioreactor fixed-bed 10 may therefore preferably serve as a single-use 3D bioreactor as further illustrated in FIG. 2. More specifically, the bioreactor 10 may be positioned in a housing 18 and then placed in the inlet and outlet compartment 20 for which inflow and outflow of fluid may be provided. Preferably, the bioreactor 10, housing 18, and the inlet and outlet compartment 20 can be fabricated as a single component using Additive Manufacturing technology. As shown in FIG. 3, the bioreactor 10 in housing 18 and inlet and outlet compartment 20 may become part of an overall 3D bioreactor system for MSCs expansion. More specifically, the 3D bioreactor is preferably positioned within a perfusion system which delivers a cell culture medium and oxygen through the 3D bioreactor for promoting cell growth. Multiple passage cell expansion methods used in 2D T-flask can also be directly applied to the 3D bioreactor except a 3D bioreactor has the cell culture area equivalent to 10 s, 100 s, or 1000 s of T-flasks.

As may now be appreciated, the 3D bioreactor herein offers a relatively large surface-to-volume ratio depending upon the diameter of the interconnected voids. By way of example, a conventional roller bottle defining a cylinder of 5 cm diameter and 15 cm height, provides a cell growth surface area of 236 cm$^2$. If the same volume is used to enclose the 3D bioreactor herein with 2.0 mm diameter interconnected voids, a total of 44,968 spherical voids can be packed into the space, which can provide a matrix with about 5,648 cm$^2$ surface area, an almost 24-fold larger than the roller bottle surface area.

At least one unique feature of the 3D bioreactor herein in comparison with hollow-fiber or microcarrier-based bioreactors is the ability to provide a large interconnected continuous surface instead of fragmented surfaces. Continuous surfaces within the 3D bioreactor herein are therefore contemplated to enable cells to more freely migrate from one area to another. Using the perfusion system shown in FIG. 3, it is contemplated that one can readily create a gradient of nutrition or cell signals inside the bioreactor to induce cell migration.

In conjunction with the preferred 3D printing technology noted herein for preparation of the 3D bioreactor, computational fluid dynamics (CFD) can now be used to simulate the medium flow inside the bioreactor and estimate the flow rate and shear stress at any location inside the 3D interconnected surface, and allow for optimization to improve the cell culture environment. More specifically, CFD was employed to simulate the flow characteristics through the 3D interconnected voids of the bioreactor herein and to estimate the distribution of: (1) flow velocity; (2) pressure drop; and (3) wall shear stress. It may be appreciated that the latter parameter, shear stress, is important for cell expansion. A reduction in shear stress can reduce or prevent shear induced cell differentiation.

Figure 4E:
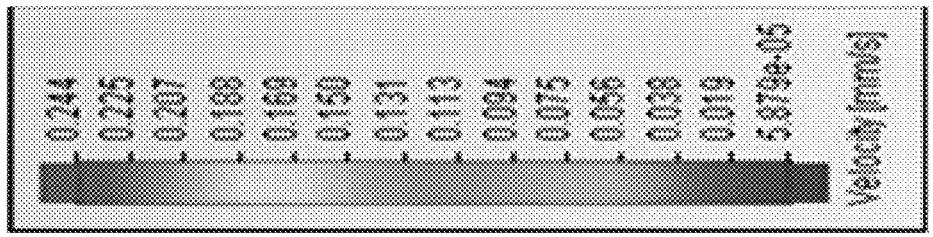
FIG. 4e indicates the scale of flow rate through a 3D bioreactor.

A small-scale (to increase computer simulation speed) cylindrical 3D bioreactor with a diameter of 17.5 mm, height of 5.83 mm, void diameter of 2 mm, and pore diameter of 0.5 mm was used in the simulations reported below. In this case, the diameter (Φ=17.5 mm) to height (H=5.83 mm) ratio of the bioreactor is 3:1 (FIG. 1*d*), which is a preferable ratio to reduce the gradient of nutrition and oxygen between the inlet and outlet of the bioreactor. Based on the cell density available on the fixed-bed spherical surface the oxygen and nutrition consumption rates were estimated, and how often the cell culture media needed to be replaced (i.e., the volume flow rate) was determined. An overall linear flow rate of 38.5 µm/sec was assumed in this simulation. Using 38.5 µm/sec rate laminar flow as the input to the 3D bioreactor, the CFD results are shown in FIGS. 4-6.

FIGS. 4*a*, 4*b*, 4*c* and 4*d* show the flow velocity profile throughout the small-scale cylindrical 3D bioreactor. FIG. 4*e* indicates the scale of flow rate. More specifically, FIG. 4*a* indicates the flow rate distribution viewed from the side of the bioreactor. The flow passes each spherical void through the pores along the flow direction. The white/gray areas in the figures are the solid regions between the spherical voids with no fluid flow. By comparing with the colored velocity scale bar in FIG. 4*e*, FIG. 4*a* indicates that the flow rate at the pores along the flow direction achieve the maximum flow rate of 200 µm/s to 240 µm/s. In contrast, the flow rates near the spherical surface reduce to a minimum of 0.06 µm/s to 19.0 µm/s, which will significantly reduce the flow caused shear stress to cells reside on the spherical surface.

Figure 4B:
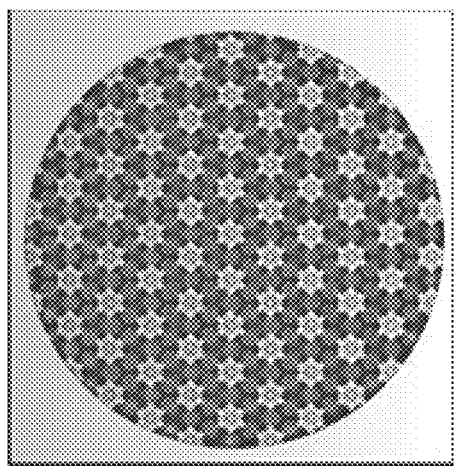
FIGS. 4a, 4b, 4c and 4d show flow rate profiles through a 3D bioreactor.

FIG. 4*b* indicates the velocity profile viewed from the top of the bioreactor through a center cross-section of the 3D structure. Again, the image shows that the maximum rates are at each center of the pores of the spherical voids along the flow direction. This maximum rate is again in the range of 200 µm/s to 240 µm/s. The flow rate near spherical surface is again low and has a value of 0.06 µm/s to 19.0 µm/s.

Figure 4D:
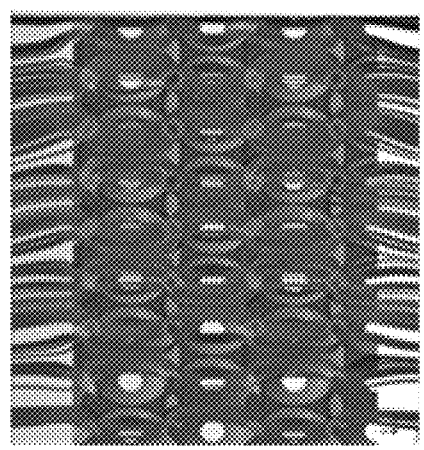
Figure 4A:
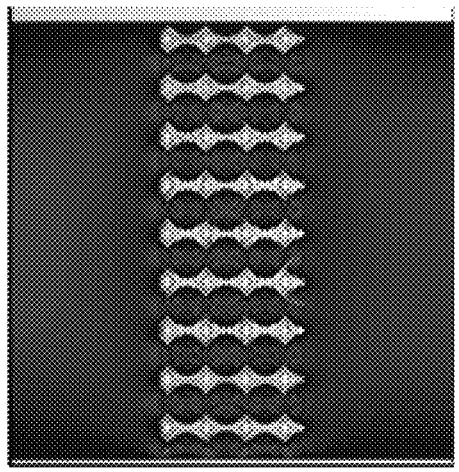
Figure 4C:
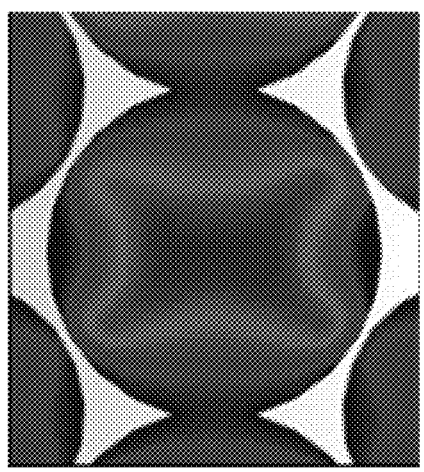

FIG. 4*c* indicates the velocity profile of an individual sphere void showing flow passing through the radial interconnected pores. FIG. 4*c* therefore provides a useful illustration of the flow distribution inside a spherical void. The high flow rate is at the central empty space of a void where there are no cells and is at a level of 200 µm/s to 240 µm/s. The cells reside on the concaved void surface where the flow rate is reduced and where the flow rate is again at a level of 0.06 µm/s to 19.0 µm/s. This unique structure can therefore shield cells from exposure to relatively high flow stress. This is another distinct advantage of the 3D bioreactor described herein over, e.g., micro-carrier based reactors, where cells are grown on the outside surface surfaces of 300 µm to 400 µm diameter microbeads with convex spherical surfaces that are suspended in a cell culture medium and stirred in a bioreactor to deliver nutrition and oxygen to the cells. Cells residing on such convex spherical surfaces can be exposed to relatively large shear stress to 0.1 Pa, which is known to affect cellular morphology, permeability, and gene expression. FIG. 4d indicates the flow trajectory through the side pores along the flow direction, indicating that the 3D bioreactor herein provides a relatively uniform flow pattern to provide nutrients and oxygen throughout.

Accordingly, the maximum linear flow rate computed inside the preferred 3D bioreactor is 200 µm/s to 240 µm/s which occurs at the 0.5 mm diameter interconnected pores between 2.0 mm diameter voids along the flow direction. As shown in FIGS. 4a-4e while the flow is preferentially in the central direction along the flow, there is still flow (~19.0 µm/sec) near the spherical surface to allow nutritional supply to the cells residing on the spherical surface. Therefore, it is contemplated that the cells are able to reside anywhere throughout the structure and thrive in any location because nutrients can be supplied both through flow convection and diffusion throughout the 3D bioreactor structure.

Figure 5B:
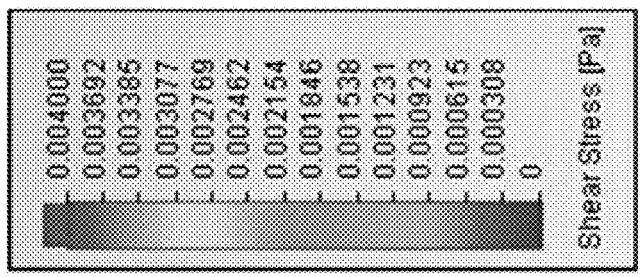
FIGS. 5a and 5b illustrate the distribution of surface shear stress in a 3D bioreactor.
Figure 5B:
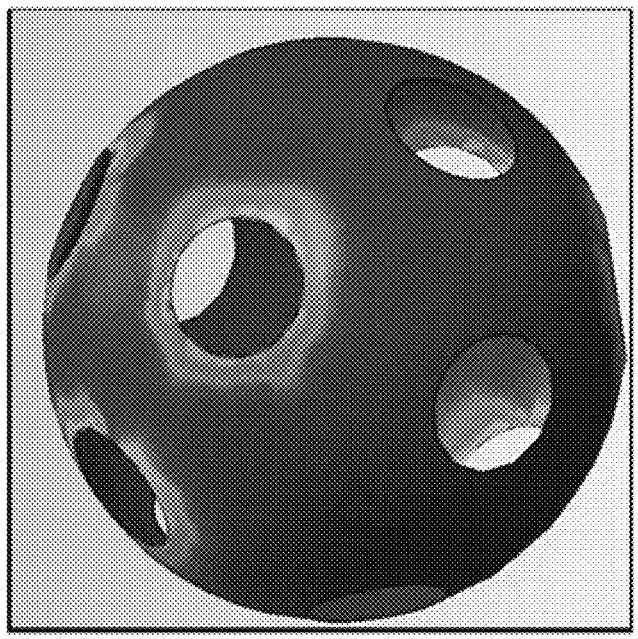
Figure 5A:
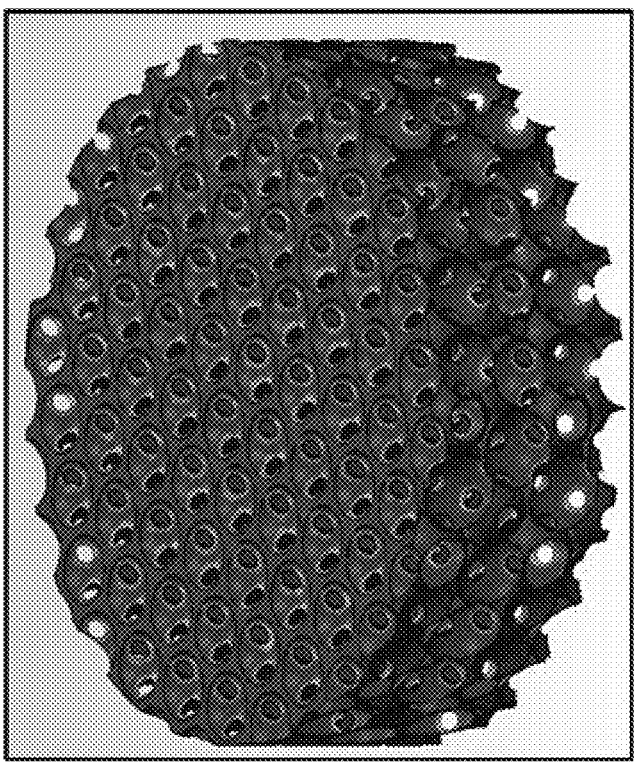

FIGS. 5a and 5b show the distribution of surface shear stress throughout the cylindrical 3D bioreactor described above as well as on a single spherical void surface. FIG. 5c indicates the scale of shear stress in units of Pa. The highest shear stress was observed on the edges of the interconnected pores. This is due to the higher flow rates at these locations. However, the majority of the useful spherical surface area within the bioreactor indicates a shear stress of less than $3 \times 10^{-4}$ Pa, which may be understood as 90% or more of the surface area of the bioreactor. This provides for cell proliferation, without shear induced differentiation. In addition, even the maximum shear stress of $4.0 \times 10^{-3}$ Pa, is believed to be lower than the average shear stress that cells experience when cultured in hollow fiber based bioreactors, wave bioreactors, and micro-carrier based bioreactors. Therefore, the 3D bioreactor herein is contemplated to provide a relatively lower shear stress environment for cell growth in comparison to existing cell expansion bioreactors. See, e.g., *Large-Scale Industrialized Cell Expansion: Producing The Critical Raw Material For Biofabrication Processes*, A. Kumar and B. Starly, Biofabrication 7(4):044103 (2015).

Figures 6A, 6B:
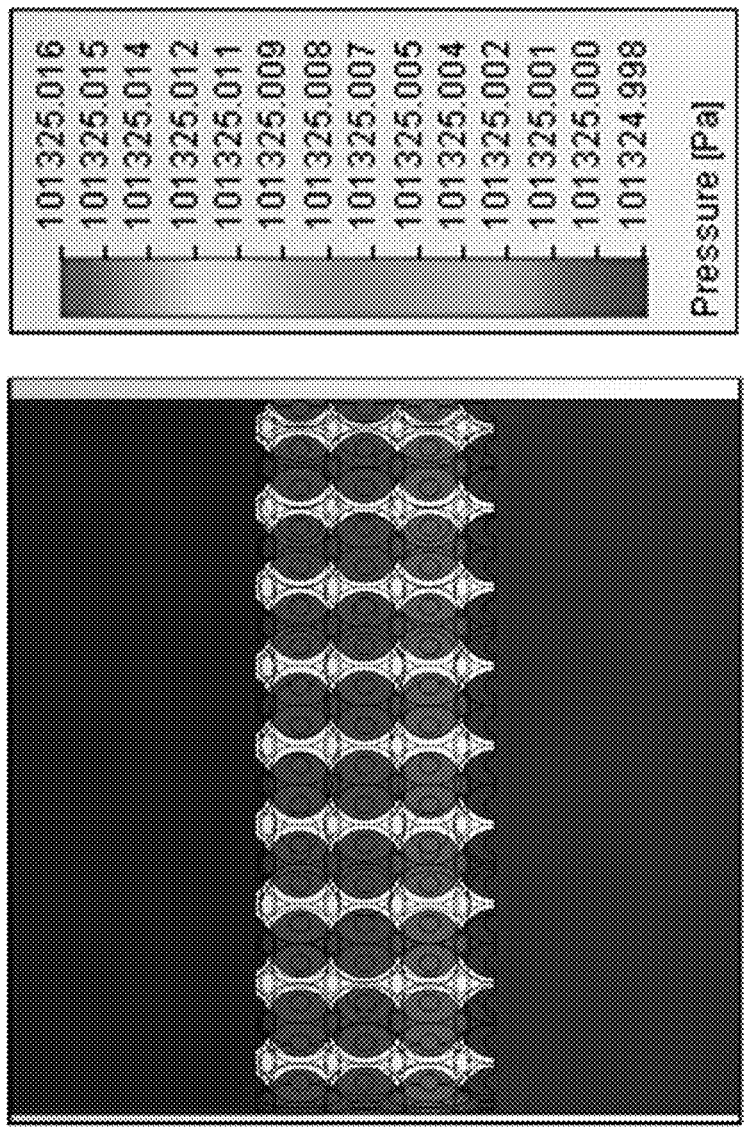
FIG. 6a illustrates the pressure drop (gradient) along the flow direction in a cylindrical 3D bioreactor.
FIG. 6b indicates a scale of pressure.

FIG. 6a illustrates the pressure drop along the flow direction from bottom to the top of the cylindrical 3D bioreactor described above. FIG. 6b provides the applicable scale of pressure. The figure indicates that the overall pressure drop between the inlet and outlet of the bioreactor is less than or equal to 1.0 Pa. The pressure drop may therefore fall in the range of 0.1 Pa up to 1.0 Pa. In other words, cells near the inlet and outlet of the bioreactor will not experience significant differences in pressure. The low gradient of pressure suggests that such design will also produce a small gradient (or difference) in nutrition/metabolites concentrations between the inlet and outlet of the bioreactor. The low gradient is due to the design of the bioreactor such that the diameter Φ is larger than the height H while the total bioreactor volume remains the same. This is superior to the hollow fiber bioreactor. It is difficult to fabricate a hollow fiber bioreactor with Φ>H ratio to reduce the gradient of nutrition/metabolites between the inlet and outlet of the bioreactor.

A comparison was also made for the same total volume cylindrical 3D bioreactor with different aspect ratios (i.e. Φ:H ratio, Φ: overall diameter of the bioreactor fixed-bed, H: overall height of the bioreactor fixed-bed). See FIG. 1d. As shown in Table 1, for the same volume flow rate (volume flow rate=cross area of flow×linear velocity), the linear velocity increases significantly for a bioreactor with a low Φ:H ratio. The increase of linear velocity also increases the surface shear stress, pressure drop, as well as the gradient of nutrition/metabolites concentrations between the inlet and outlet, which would have an unfavorable effect for cell expansion. The disclosed fixed-bed 3D bioreactor is therefore preferably designed into a Φ:H ratio structure, e.g., a Φ:H ratio in the range of greater than 1:1 and up to 100:1. Preferably, the Φ:H ratio is greater than 1:1 and up to 10:1.

TABLE 1

Flow Rate Comparison For 3D Bioreactor With Different Aspect Ratios

| # | Ratio (Φ:H) | Diameter (Φ) (cm) | Height (H) (cm) | Flow Rate (µm/sec) |
|---|---|---|---|---|
| 1 | 3:1 | 10.5 | 3.5 | 38.5 |
| 2 | 1:1 | 7.5 | 7.5 | 75.4 |
| 3 | 1:3 | 5 | 15 | 169.8 |

Figure 7B:
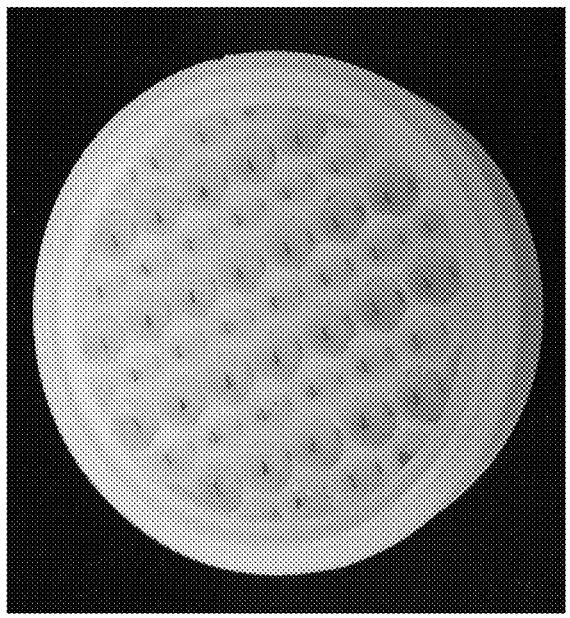
FIG. 7b illustrates the 3D bioreactor fixed-bed together with a bioreactor chamber.
Figure 7D:
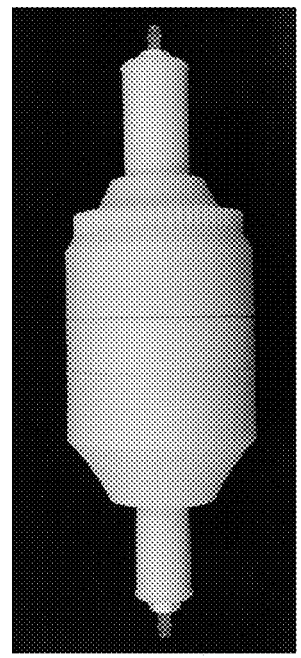
FIG. 7d illustrates an assembled 3D bioreactor.
Figure 7A:
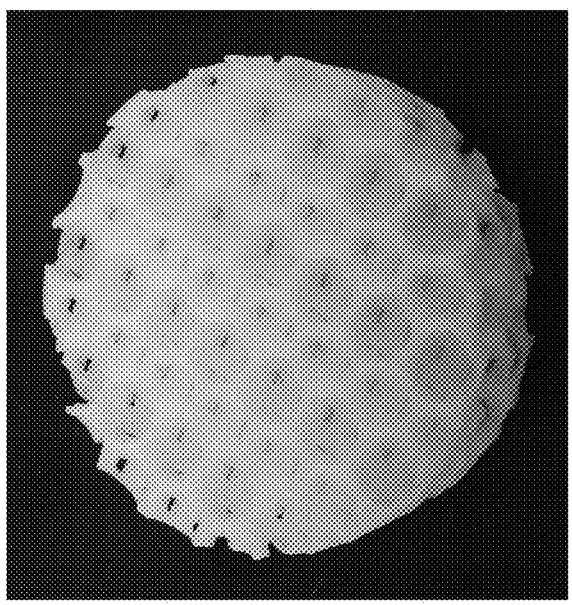
FIG. 7a illustrates a 3D bioreactor fixed-bed generated by FDM 3D printing.
Figure 8:
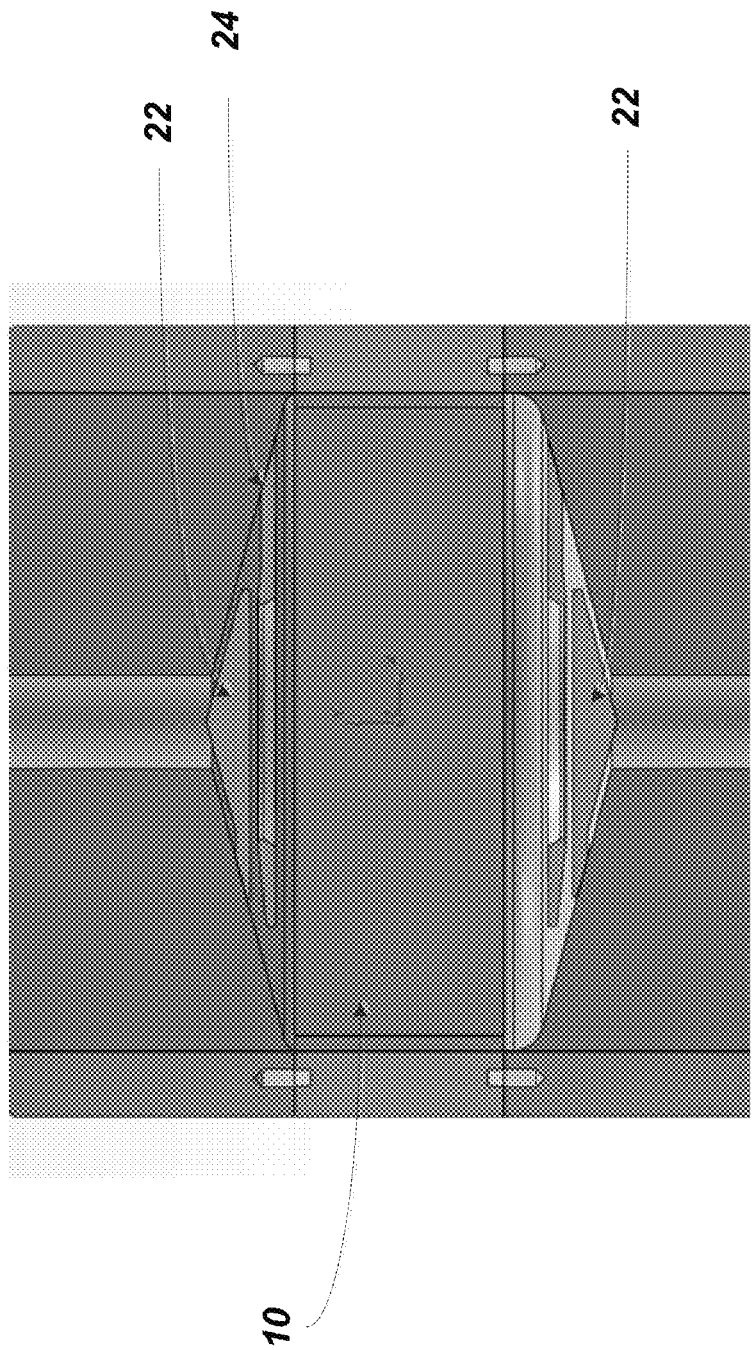
FIG. 8 illustrates two fluid distributors placed at the inlet and outlet of the 3D bioreactor to approach a laminar flow.

FIG. 7a illustrates a 3D bioreactor fixed-bed part generated by FDM 3D printing with interconnected 6 mm diameter voids and 1 mm interconnected pores. This 3D bioreactor was printed with ABS filament. The diameter (Φ) and height (H) of this particular 3D bioreactor is 4.28 cm and 1.43 cm respectively. Accordingly the Φ:H ratio is 3:1. There are about 134 interconnected open-voids included in the fixed-bed. The total interconnected continuous spherical surface area $SA_u$ for cell culturing is about 152 cm$^2$. The inlet and outlet wall and fluid distributor 22 at the inlet and outlet (FIG. 8) provides an additional 88 cm$^2$ surface area for cell culturing. In other words, there is about 240 cm$^2$ total useful surface area in the 3D bioreactor for cell attachment. The fluid distributor can improve the laminar flow through the bioreactor. The fluid distributor is optional if the Reynolds number is <2100 or in the range of greater than 0 up to and not including 2100.

Figure 7C:
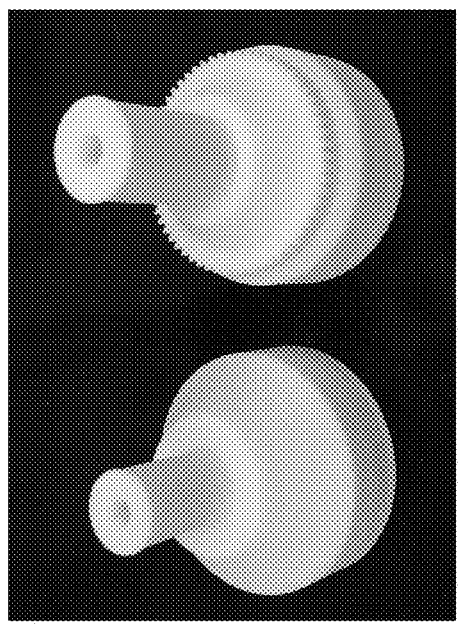
FIG. 7c illustrates the inlet and outlet of a 3D bioreactor.
Figure 7F:
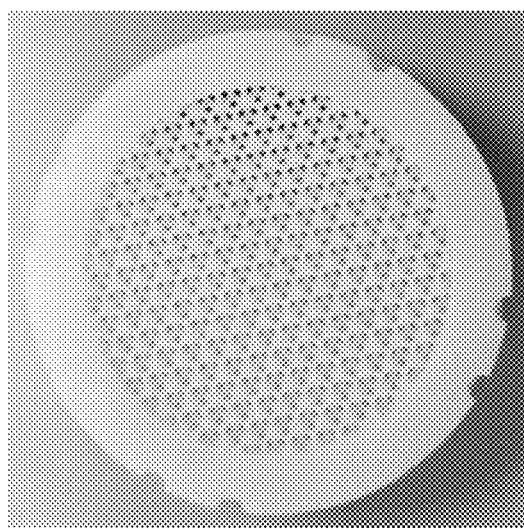
FIG. 7f illustrates a 3D bioreactor fixed bed generated by DLP 3D printing.
Figure 7E:
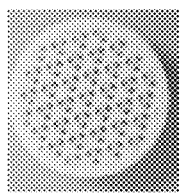
FIG. 7e illustrates a 3D bioreactor fixed-bed generated by SLA 3D printing.

FIG. 7b shows that the fixed-bed of the 3D bioreactor was solvent bound into a bioreactor chamber. This will seal the gaps between the fixed-bed and the chamber wall, which will force the perfusion cell culture medium to pass through the interconnected pores instead of through those gaps. Preferably, the fixed-bed and chamber is printed together as an integrated part to increase the manufacturing efficiency. FIG. 7c illustrates the inlet and outlet of the bioreactor. They are designed geometrically to promote a laminar flow through the fixed-bed. The inlet of the bioreactor optionally contains a built-in rotation gear, which may be coupled to a stepper motor to control the rotation of the bioreactor for uniform cell seeding (see below). The integrated bioreactor is shown in FIG. 7d and is able to connect to ⅛ inch tubing to conduct the fluid flow. Alternatively, the inlet and outlet can be made for repeated usage, where only the inside bioreactor fixed bed is disposable. Also shown in FIG. 7e is a relatively smaller-size 3D bioreactor fixed bed produced by DLA 3D printing having a 3.0 mm void and a 0.5 mm pore. FIG. 7f is a relatively larger-size 3D bioreactor fixed bed using DLP 3D printing having the same-diameter 3.0 mm void and a 0.5 mm pore. When scaling up the bioreactor, the internal structure of the bioreactor is maintained. Therefore, the perfusion volume flow rate can be scaled up proportionally while keeping the local linear flow rate the same. In this way, minimum process change is required during the scale-up process which can reduce the process development costs.

Figure 9:
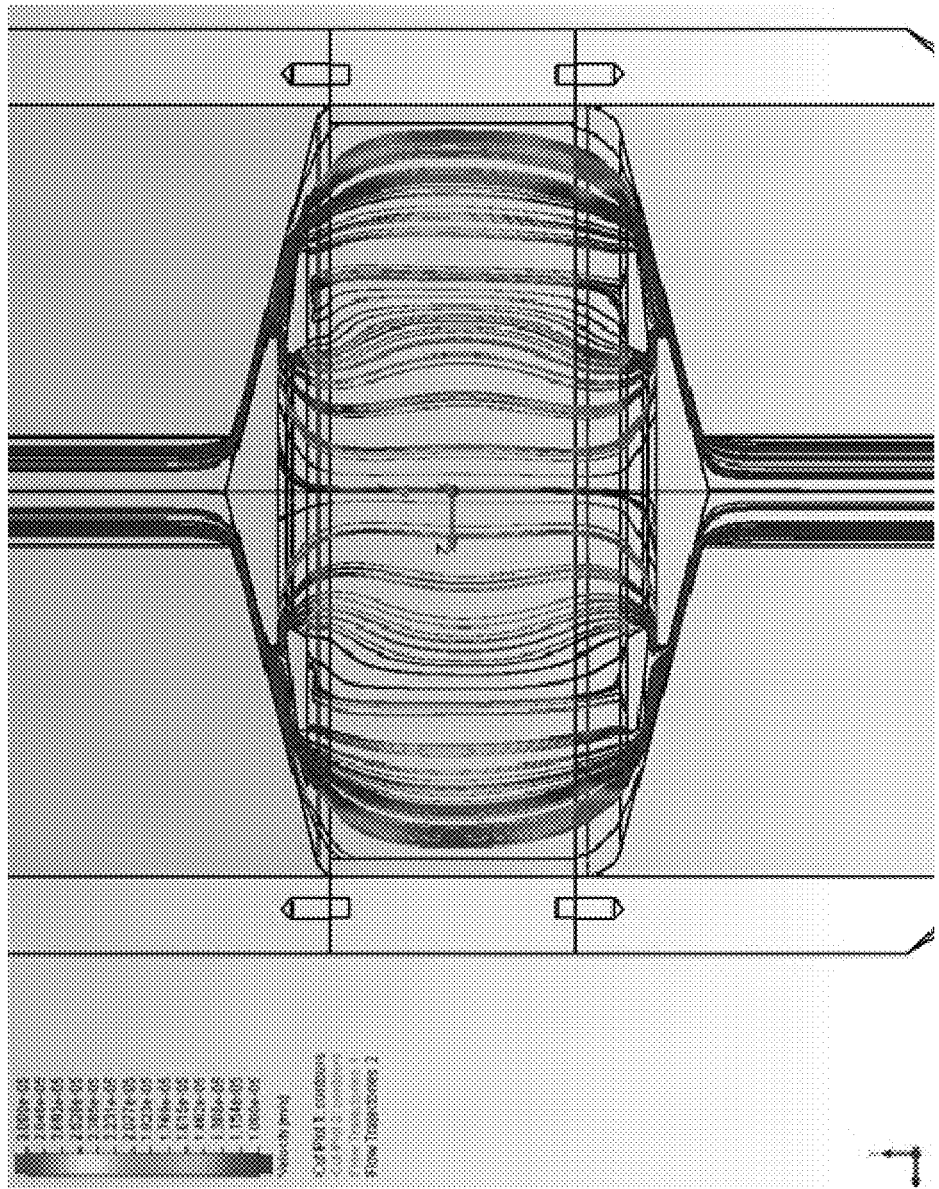
FIG. 9 illustrates a flow rate profile through the 3D bioreactor when using the fluid distributor.

It should next be noted that the fluid distributor 22 (FIG. 8) is preferably such that it will improve the flow uniformity through the 3D bioreactor. The design of the inlet, outlet, and fluid distributor also preferably takes into consideration the following: (1) improve the flow uniformity through the 3D bioreactor; (2) minimization of the dead-volume 24 at inlet and outlet to reduce the overall priming volume of the bioreactor; and (3) preventing bubble collection inside the bioreactor. FIG. 9 shows the flow velocity profile throughout the 3D bioreactor based on CFD simulation by using the fluid distributor. The use of the fluid distributor (FIG. 8) improved the uniformity of the flow. The maximum flow rate (around 30 µm/s) and the minimum flow rate (around 10 µm/s) are relatively close to each other and serve to promote uniform laminar flow (i.e. flow of fluid in relatively parallel layers). A relatively uniform flow rate everywhere in the bioreactor will also provide smaller differences of shear stress to cells residing at different locations in the bioreactor.

The 3D bioreactor can be fabricated by other additive manufacturing technologies such as selective laser sintering (SLS), stereolithography (SLA), Digital Light Processing (DLP), and etc. FIGS. 7e, 7f.

Figure 10B:
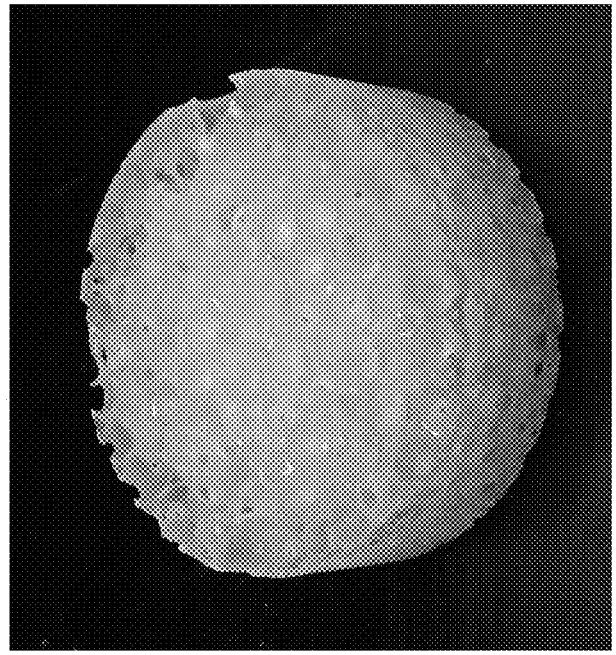
FIGS. 10a and 10b illustrate the formation of a 3D bioreactor by the alternative porogen-leaching method.
Figure 10A:
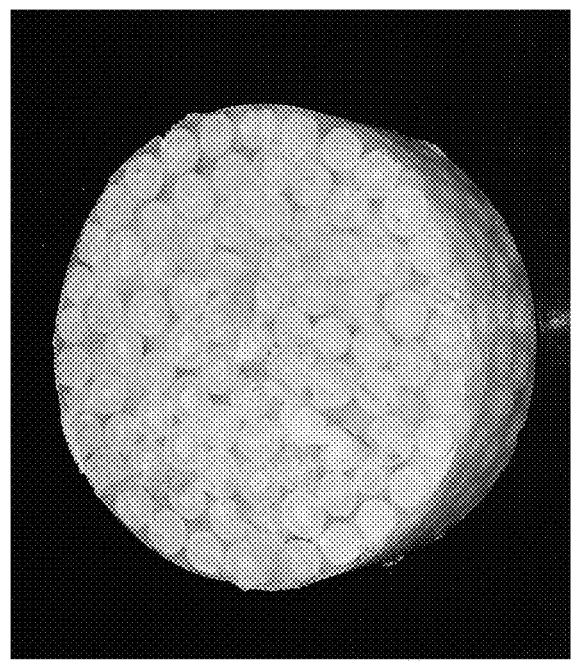

In addition to preparing the 3D bioreactor herein via additive manufacturing or 3D printing, it is contemplated that the 3D bioreactor may be prepared by the traditional porogen-leaching method to provide an interconnected cell culture surface. FIGS. 10a and 10b shows a 3D bioreactor utilizing a porogen-leaching methodology. This is reference to combining porogen and polymer in a mold, followed by leaching out of the porogen to generate pores. The 3D bioreactor in FIG. 10a starts with the step of tightly packing 4.0 mm water-soluble spherical sugar beads (as porogen) in a cylindrical stainless mold by shaking, tapping, and pressing the beads, so that the beads are in contact. The gaps between the beads are filled with acetone containing 5.0% by weight deionized water. This is followed by evaporation the acetone and water under vacuum chamber overnight. The gaps between the beads are then filled with a low viscous polymerizable vinyl monomer such as styrene together with polymerization initiators such as benzoyl or tert-butylperoxybenzoate. The styrene monomer will then polymerize to form polystyrene. The sample remained at 90° C. for 8-12 hours, and then was heated to 115° C. for an additional 3 hours and removed from the oven to provide what is illustrated in FIG. 10a. The sugar beads were then leached out while submerged in an ultrasound water bath to leave the polystyrene 3D bioreactor fixed-bed with interconnected voids. See FIG. 10b. The 3D bioreactor is then extracted with methanol for three days to remove any residual styrene monomer. However, the porogen leaching method not only has a complex manufacturing process, but also is difficult to achieve exact reproducible structures since the packing of porogen beads is a random process.

For the 3D printed bioreactor (FIG. 7d) using ABS or PMMA, the hydrophobic internal surfaces of the bioreactor are preferably modified to allow for cell adherence. Polydopamine was used as a primer coating to the bioreactor surfaces so that other proteins can be easily adhere to the bioreactor surface via the polydopamine coating. It therefore can be noted that the polydopamine primer coating can be combined with other coatings such as peptides, collagen, fibronectin, laminin, multiple cell extracellular matrix proteins or selected antibodies that are required by particular cell types.

Incubation of the bioreactor surface in a 0.25 mg/mL dopamine dissolved in 10 mM Tris buffer (pH=8.5 at 25° C.) for a period of about 18 hours, resulted in an effective polydopamine layer for the subsequent protein coating. After polydopamine is deposited on the bioreactor surface, other proteins can then bind with functional ligands via Michael addition and/or Schiff base reactions. The ligand molecules therefore include nucleophilic functional groups, such as amine and thiol functional groups.

It can also be appreciated that when the bioreactor herein is coated with substituted or unsubstituted poly(p-xylene), polydopamine may be similarly applied over the substituted or unsubstituted poly(p-xylene) coating to similarly allow for cell adherence. Again, the polydopamine may then provide a coating surface so that other proteins can adhere via the polydopamine coating over the poly(p-xylene) coating. Such binding is again contemplated to rely upon protein binding via functional ligands via Michael addition and/or Schiff base reactions and the ligand molecules can again include nucleophilic functional groups, such as amine and thiol functional groups. It can therefore more generally be understood that the polydopamine coating is such that it is capable of binding additional layer or layers for cell culturing via the use of functionalized ligands.

It should now be appreciated from all of the above that one of the additional features of the 3D bioreactor disclosed herein is that one may now design a 3D bioreactor, with particular geometric and void volume requirements, and corresponding available surface area requirements, and be able to achieve (i.e., during fabrication or manufacturing) such targets with relatively minimal variation. For example, one may now identify a design requirement for a 3D bioreactor wherein the one or more internal voids are to have a targeted void volume "$V_t$", and the 3D bioreactor itself is to have a targeted overall surface area for cell culturing "$SA_t$". Accordingly, one may now form such 3D bioreactor wherein the one or more internal voids have an actual void volume "$V_a$" that is within +/−10.0% of $V_t$, or more preferably, +/−5.0% of $V_t$. Similarly, the actual surface area for cell culturing $SA_a$ is within +/−10.0% of $SA_t$, or more preferably +/−5.0% of $SA_t$. Moreover, one may also identify for the internal surface within the targeted voids a targeted geometry for fabrication such as a targeted radius of curvature "$Rc_t$" and then in fabrication the actual radius of curvature "$Rc_a$" of the void internal surface can now be achieved that is within +/−5% of $Rc_t$.

Post Printing Process

Figure 18:
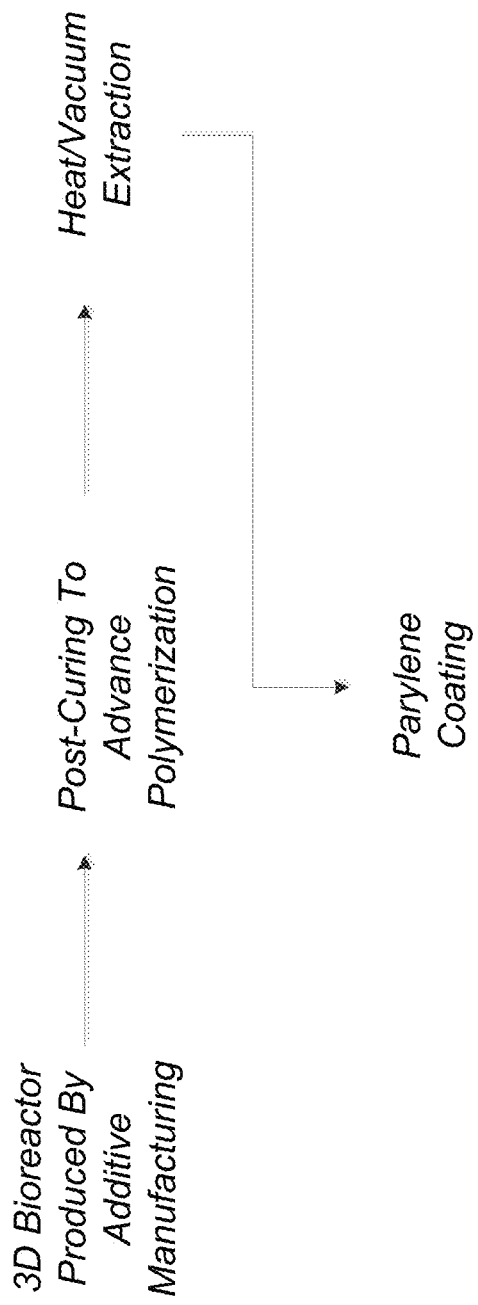
FIG. 18 illustrates a preferred post-printing protocol for the 3D bioreactor herein.

The 3D bioreactor herein is now preferably subjected to additional post-printing procedures. Such procedures are designed to provide the ability to reduce or prevent leaching of any residual monomers and/or photoinitiators that may otherwise have been employed for 3D bioreactor printing. Such may particularly be the case when the additive manufacturing procedures involve stereolithography (SLA) or digital light processing (DLP) which involves curing (polymerization) of a liquid resin. Attention is therefore directed to FIG. 18 which summarizes a preferred post-printing protocol. As illustrated, the 3D bioreactor herein produced by additive manufacturing that initially relies upon photo-polymerization (light-induced polymerization) is now preferably post-cured, preferably by additional exposure to UV light. Such additional exposure to UV light is contemplated to increase the underlying polymerization during printing and/or to reduce the level of relatively low molecular weight material, such as un-polymerized monomeric material. In addition, one may now follow such post-curing with treatment of heat and/or vacuum to further reduce or remove such relatively low molecular weight material. For example, one may apply a vacuum of $10^{-3}$ Torr or lower at temperatures from ambient to 125° C. It is therefore contemplated that by use of post-curing, alone or in combination with vacuum and/or heating, one may reduce the level of relatively low MW material (MW of less than or equal to 500) to less than or equal to 2.0% by weight, more preferably to a level of 0.01% by weight to 1.50% by weight, and even more preferably 0.01% by weight to 0.75% by weight.

In addition, it is contemplated herein that for any given bioreactor produced herein, it may now be preferably subject to a coating procedure to similarly reduce and/or eliminate the leaching of the aforementioned relatively low molecular weight compounds that are otherwise toxic to living cells. Such coatings may also be selectively functionalized to promote adherent cell attachment and growth. Preferably, the coating procedure relies upon the use of parylene monomers, e.g., [2.2]paracyclophanes, that may be functionalized with identified $R_1$, $R_2$, $R_3$ and $R_4$ groups according to the following general reaction scheme, wherein the indicated polymerization is promoted by exposure to heat (~550° C.) under vacuum to provide a substituted or unsubstituted poly(p-xylylene) polymer structure. It should be appreciated that in the scheme below, the start of polymerization is initiated by a ring opening at elevated temperature in the gas phase prior to deposition on the 3D bioreactor which is preferably maintained at relatively lower temperature (e.g., ≤100° C.):

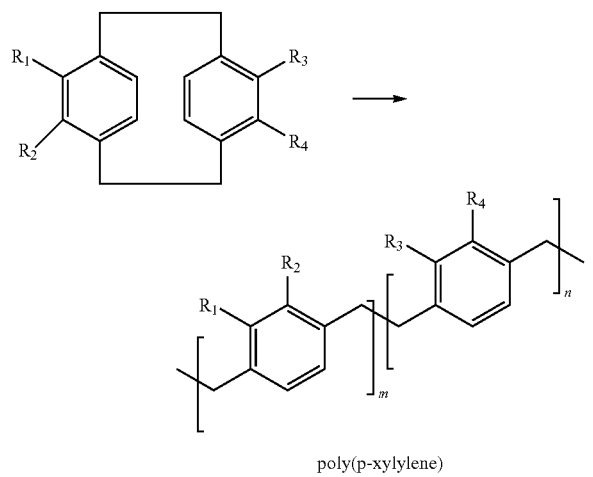

poly(p-xylylene)

In the above, when one of the R groups per repeat unit "m" and/or repeat unit "n" is chlorine, and the other R group is a hydrogen, the above represents the polymerization of parylene C. It is a USP Class VI and ISO-10993-6 certified biocompatible material. The values of "m" and "n" of the identified repeating units are such that molecular weight values are relatively high, such as ~500,000. It is therefore contemplated that the use of the parylene monomers and ensuing polymeric coatings are such that one may now coat the entire 3D bioreactor herein with an impermeable film. The film may preferably have a thickness between 200 Angstroms to 100.0 μm. It may be appreciated that $R_1$, $R_2$, $R_3$, and $R_4$ may be selected from hydrogen, a halogen (—Cl or —Br) as well as other functional groups such as amines (—$NH_2$), aliphatic aldehydes (—CHO), carboxylic acid functionality (—COOH), hydroxyl (—OH) or carboxylate functionality as in —$C(O)CF_3$. One may also initially coat with a first layer of parylene C followed by a coating of a different parylene, e.g., wherein $R_1$, $R_2$, $R_3$, and $R_4$ may then be selected from an amines (—$NH_2$) and/or aldehyde (—CHO) functionality. Accordingly, one may provide polymeric coatings for the 3D bioreactor herein, wherein the coating comprises a plurality of layers, each with its own particular and different chemical composition (i.e. the identity of at least one of $R_1$, $R_2$, $R_3$, and $R_4$ are different between at least two of the layers).

It is further contemplated that the 3D bioreactor with a functionalized coating of an aldehyde can undergo reaction with, e.g., antibody proteins (e.g. anti-CD3/28) with end flexible tethers that are amino terminated (or other organic terminal group) of an oligoethylene oxide (OEG) of different lengths. In other words, the use of poly(ethylene oxide) type tethers that include functional terminal groups such as an amine group, as in:

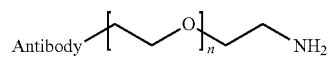

where the value of n may be in the range of 1-200, and which may then bind to the functionalized parylene coating on the 3D bioreactor herein as follows, where one binding reaction site is illustrated and where it should be appreciated that multiple binding reactions may take place depending upon regulation of the reaction parameters (e.g. temperature and time to increase binding reaction yield):

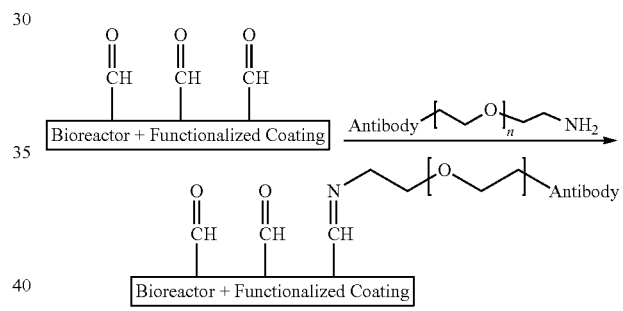

As may therefore be appreciated, in the above, one may vary the surface mobility of the cell stimulating protein to enable better binding with the targeted, cell surface receptors and minimize non-specific protein or other macromolecule physical absorption from the cell culture media.

In another contemplated embodiment, biotin, with an end functionalized tether, can be bound to the functionalized parylene coating in a first step. In a second step the biotin end group can be complexed with avidin or streptavidin. In a third step the biotin-strepavidin complex is then bound to the biotin functionalized stimulatory antibody to complete the functional surface appropriate for cell stimulation.

Figure 11:
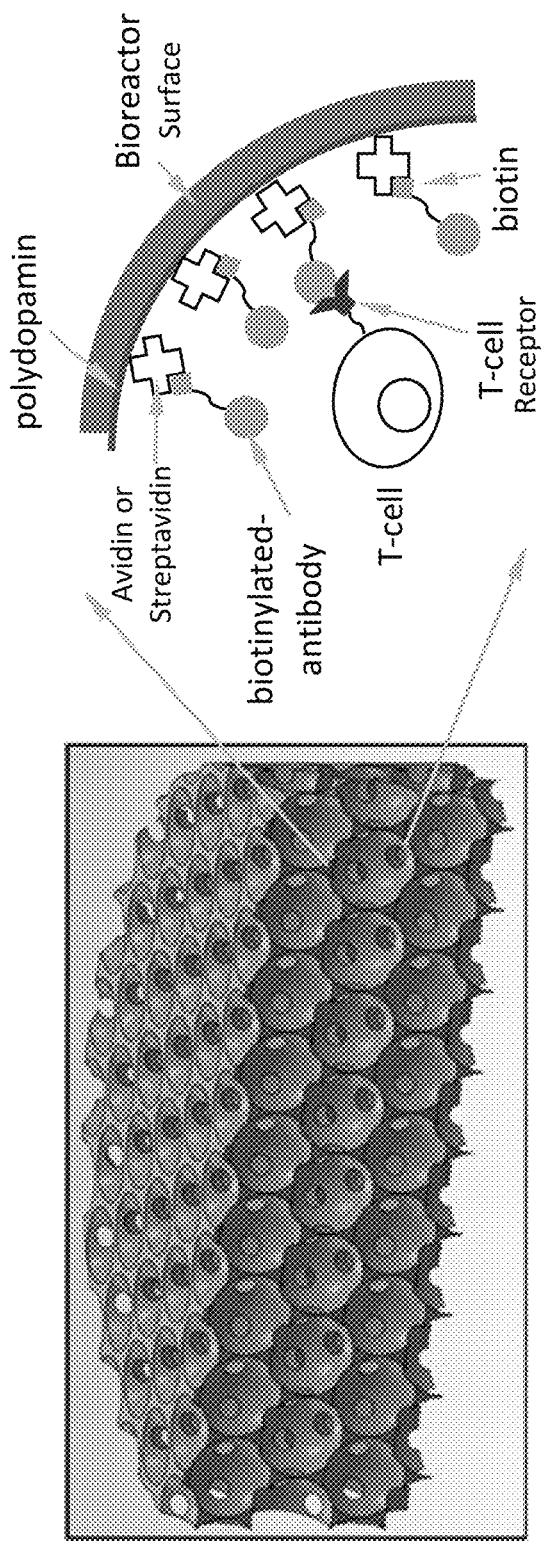
FIG. 11 illustrates immobilization of antibodies on the 3D bioreactor's spherical void volume for binding and activation of T-cells.

The present invention advances further on the use of the above referenced 3D bioreactor herein, to provide for T-cell expansion as applied for immunotherapy purposes. Reference is made to FIG. 11, which illustrates immobilization of antibodies on the bioreactor's spherical void volume surface for binding and activation of T-cells. More specifically, for the 3D bioreactor, one can now immobilize antibodies (biotin conjugated sphere-shaped proteins) such as anti-CD3 and anti-CD28 antibodies on the bioreactor surface via the biotin-avidin/streptavidin binding mechanism. Avidin or streptavidin are pre-coated on the bioreactor surface through the prime polydopamine coating as discussed above. More specifically, after a polydopamine coating is applied to the surface of the 3D bioreactor herein, which as noted already can include a poly(p-xylene) coating, one may attach a tetrameric protein (protein with quaternary structure of four subunits) such as avidin or streptavidin, which have affinity for biotin. Accordingly, it may be appreciated that the polydopamine coating provides the ability to make the bioreactor surface relatively more hydrophilic and for attachment of proteins and antibodies where by contrast, the poly(p-xylene) coating serves to block monomer leaching and to reduce or avoid cytotoxicity. Accordingly, proteins with quaternary structure (avidin or streptavidin) may be relied upon to immobilize biotinylated antibodies, for example, anti-CD3 antibody onto the bioreactor surface. A biotinylated antibody is reference to covalent attachment of biotin to the antibody. When T-cells flow through the bioreactor, they will bind and activate via the T-cell surface receptor, for example CD3, via the CD3, anti CD3 antibody binding. This is then followed by exposing the activated T-cells to a perfusion media containing a signaling molecule to provide T-cell expansion. The signaling molecule may preferably include a cytokine signaling molecule such as interleukin-2 IL-2). It should be noted, however, that in the broad context of the present invention, it is contemplated that one may exclude the need for the use of a polydopamine coating and immobilize the antibody (e.g. the anti-CD3 antibody) directly on the surface of the 3D reactor, avidin/streptavidin directly on the bioreactor surface to bind biotinylated antibodies.

Figure 12:
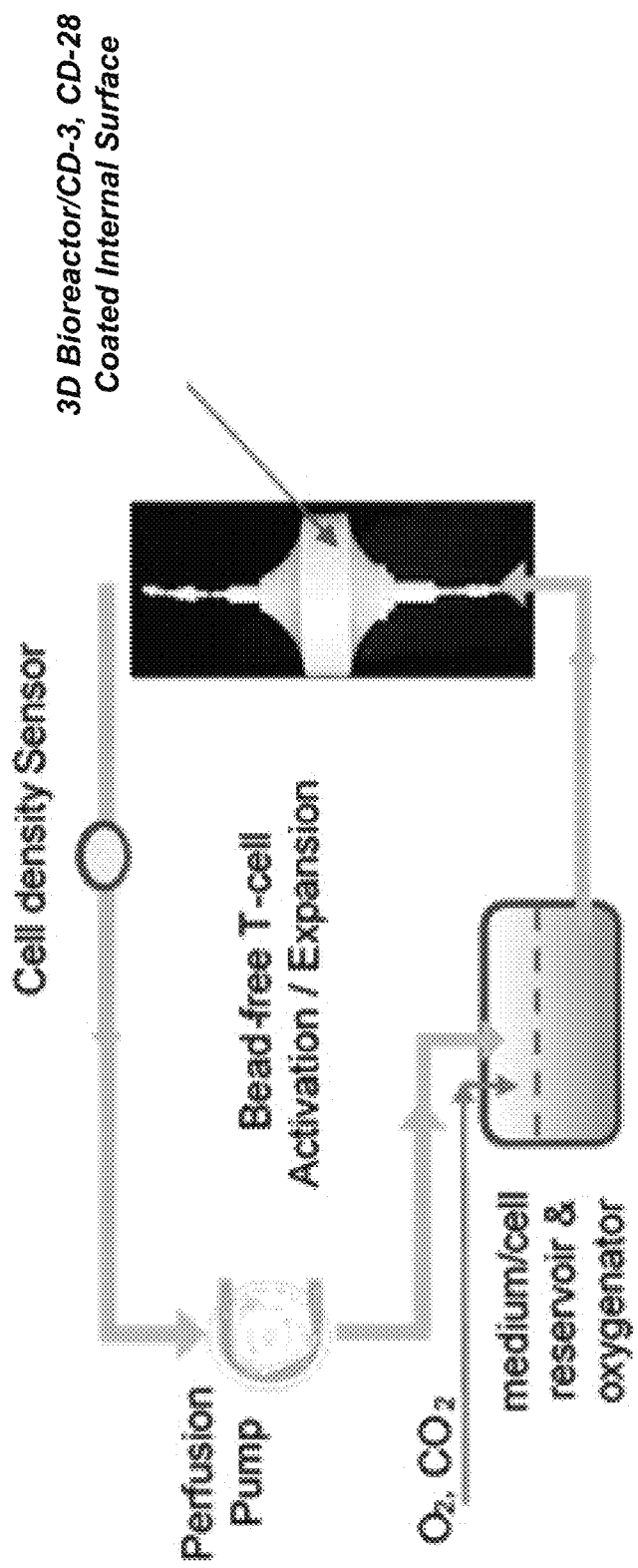
FIG. 12 illustrates a bead-free, closed loop perfusion based 3D bioreactor for T-cell activation and expansion.

Using the 3D bioreactor herein, a closed-loop perfusion-based system for T-cell expansion is now possible as illustrated in FIG. 12. More specifically, FIG. 12 illustrates a bead-free, closed-loop perfusion based 3D bioreactor for T-cell activation and expansion. The perfusion system preferably contains a cell-safe peristaltic pump and a medium/cell reservoir, which is able to add media to dilute cell density for more effective cell expansion or exchange media to maintain the nutrient concentration during the expansion process. The medium reservoir may also serve as an oxygenator with gas infusion and stirring or shaking mechanism to mix the nutrients and oxygen. The suspended T-cells in the medium perfused through the 3D bioreactor have many chances of contacting CD3 and CD28 antibodies on the spherical surfaces and thus to be activated. The immobilized CD3 and CD 28 on the large surface is expected to provide equivalent stimulation to T-cells as the magnetic beads used in the current T-cell expansion system. Without the beads, the processes will be simplified significantly. In addition, this closed-loop system facilitates automation and cost-effective cGMP cell manufacturing.

Table 2 lists the dimensions, culture surface area, number of magnetic beads with equivalent total surface area, expected medium volume, etc. of three different sized bioreactors. PMMA, an FDA approved implantable biocompatible material, was used to fabricate the bioreactor using a DLP 3D printer. Table 2 also lists the approximate material cost to construct the identified 3D bioreactors.

TABLE 2

Dimension and Cost of Fabricating Different Sized
3D Bioreactors Using SLA/DLP 3D Printing

| PBMC Seeding Capacity | $2.5 \times 10^{7\alpha}$ | $2.2 \times 10^8$ | $2.2 \times 10^9$ |
|---|---|---|---|
| Bioreactor diameter (cm) | 2.1 | 4.2 | 9.0 |
| Bioreactor height (cm) | 0.7 | 1.4 | 3.0 |
| Surface area (cm²) | 29 | 250 | 2500 |

TABLE 2-continued

Dimension and Cost of Fabricating Different Sized
3D Bioreactors Using SLA/DLP 3D Printing

| PBMC Seeding Capacity | $2.5 \times 10^{7\alpha}$ | $2.2 \times 10^8$ | $2.2 \times 10^9$ |
|---|---|---|---|
| Area equivalent to # of beads | $7.5 \times 10^7$ | $6.5 \times 10^8$ | $6.5 \times 10^9$ |
| Medium volume (mL) | 2 | 14 | 136 |
| Build material volume (mL) | 0.78 | 5.4 | 53.6 |
| Material cost$^\beta$ | $0.20 | $1.34 | $13.4 |

Figure 13:
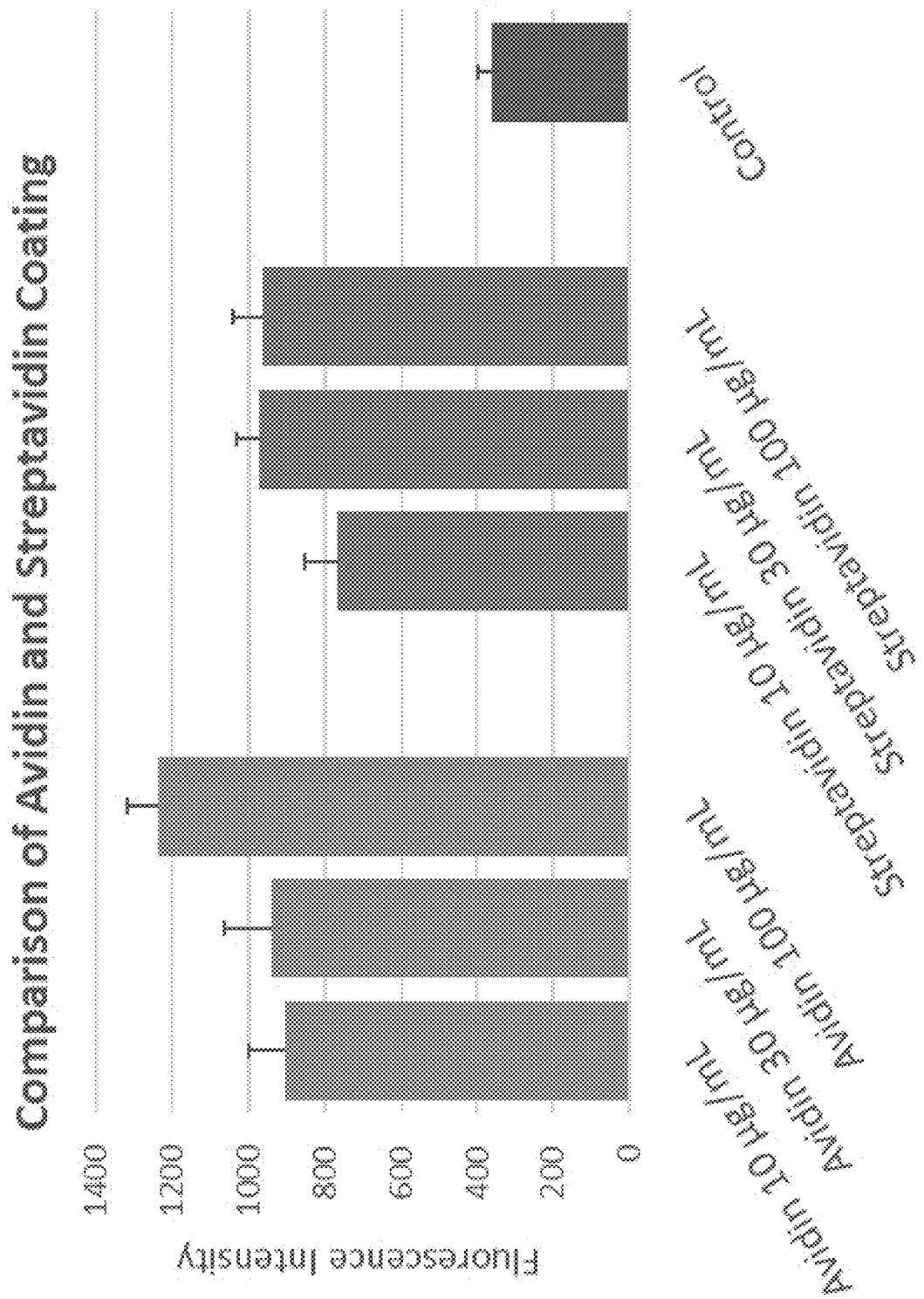
FIG. 13 illustrates fluorescence intensity of avidin and streptavidin coatings at different concentrations. The fluorescent-labeled avidin and streptavidin were used to show the concentration of avidin and streptavidin coated on the bioreactor surface.

$^\alpha$based on 3:1 beads:cells ratio
$^\beta$matrix only, does not include bioreactor's inlet and outlet; also assume 3 mm diameter hollow sphere and 0.5 mm pore size Coating of Avidin (or Streptavidin) on the Bioreactor Surface To mimic the Miltenyi MACSiBead system, avidin (streptavidin) and biotin binding mechanism was employed to immobilize anti-CD2, CD3 and CD28 antibodies on the polydopamine coated bioreactor surface. First, different concentrations of fluorescence-labeled avidin and streptavidin were tested (FIG. 13) and 100 µg/mL of avidin or 30 µg/mL of streptavidin was found to achieve a relatively high avidin or streptavidin coating density on the bioreactor surface. FIG. 13 shows florescence intensity of avidin and streptavidin coating at difference concentrations. The fluorescent-labeled avidin/streptavidin were used to test the concentration of avidin or streptavidin that can be bound on to the polydopamine prime coating. A preferred procedure of avidin/streptavidin coating is described as follows. The coating concentration of avidin or streptavidin can be further optimized:

1) The bioreactor surfaces are first coated by polydopamine herein.
2) Dissolve avidin or streptavidin in TRIS buffer (pH 8.5) to prepare the coating solution, with the avidin or streptavidin concentration of 100 µg/mL or 30 µg/mL, respectively. Immerse the bioreactor into the coating solution for 12 hours, while gentle shaking in the dark.
3) Wash the scaffolds thoroughly with phosphate-buffered-saline (PBS). Then leave the scaffolds in PBS, ready for coating with biotinylated antibodies.

Figure 14:
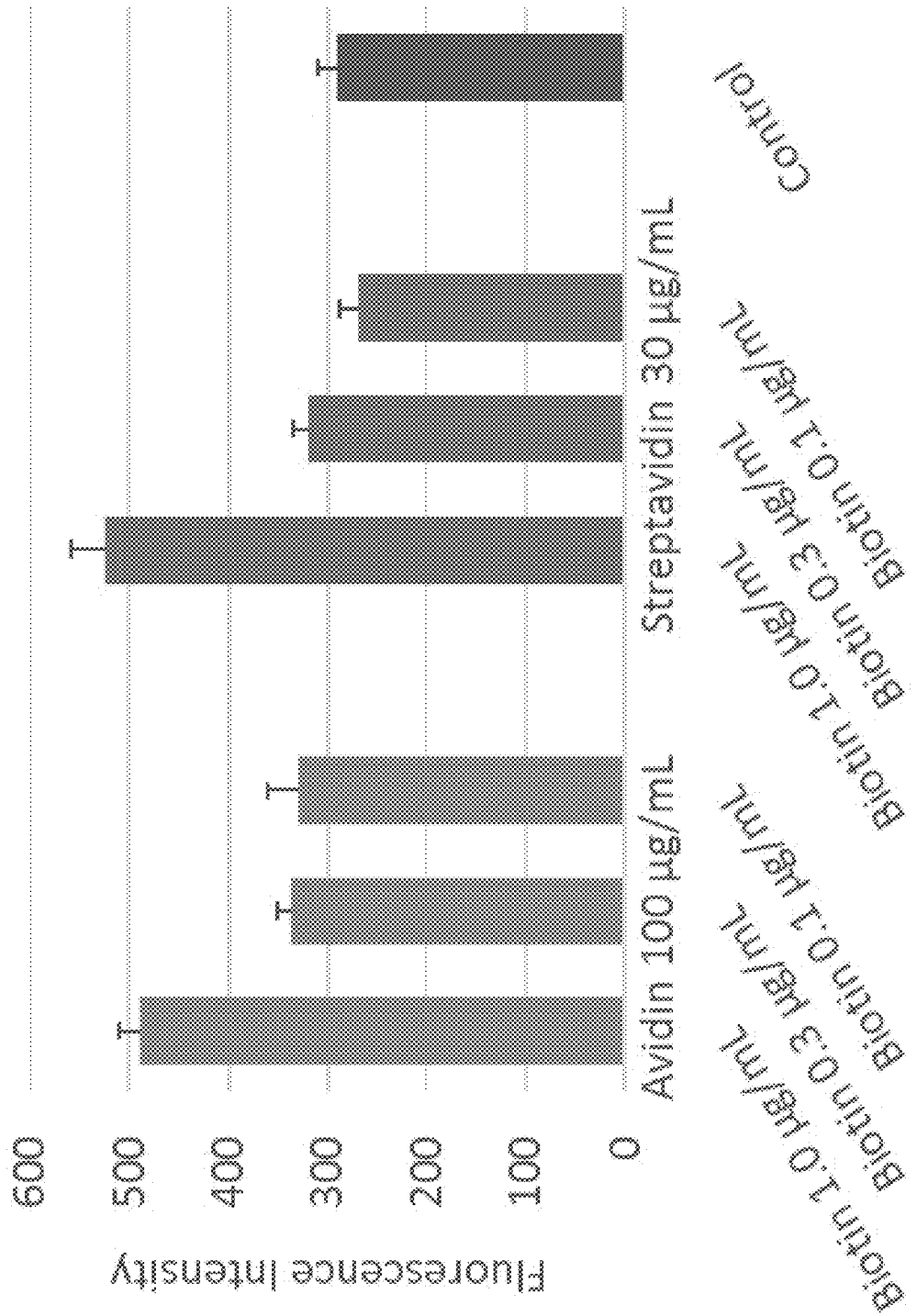
FIG. 14 illustrates fluorescence intensity of the biotin coating on avidin or streptavidin. The fluorescent-labeled biotin was used to show the concentration of biotin bound onto the avidin or streptavidin.

A comparison was then run with respect to different concentrations of fluorescence-labeled biotin as a second layer coating to bind to the avidin or streptavidin base layer (FIG. 14). 1.0 µg/mL of biotin was identified as successfully binding to the immobilized avidin or streptavidin. See FIG. 14, which identifies fluorescence intensity (proportional to biotin concentrations) of the biotin coating on avidin or streptavidin. After confirming that biotin can successfully bind to the bioreactor surfaces coated with avidin or streptavidin, biotinylated anti-CD2, CD3, and CD 28 antibodies were applied onto the bioreactor for T cell activation and expansion.

To preferably apply the antibody coating on to the 2.1 cm diameter scaffolds (i.e., equivalent to about $7.5 \times 10^7$ beads total surfaces):

1) Remove the bioreactor scaffolds from the BPS
2) Remove as much PBS from the scaffolds as possible, but do not let the scaffold dry.
3) Combine the 200 µL of 100 µg/mL CD2-Biotin, 200 µL of 100 µg/mL CD2-Biotin, and 200 µL of 100 µg/mL CD28-Biotin in a 15-mL tube, add 1.4 mL of antibody labeling buffer (PBS without Ca2+ and Mg2+, pH=7.2 plus 0.5% heat-inactivated fetal bovine serum and 2 mM EDTA), and mix well to make a total 2 mL biotinylated antibodies, with the concentration of each antibody being 10 μg/mL.
4) Add 2 mL of the mixed antibodies to cover a bioreactor matrix (without inlet and outlet, FIG. 7e) in a 12 well plate, pipette up and down to mix.
5) Incubate in matrix in the dark in the refrigerator for 2 hours under gentle shaking at a temperature of 2° C. to 8° C.
6) Remove the unbound antibodies from the scaffold thoroughly with PBS wash.

The coating procedures using polydopamine, avidin/streptavidin, and biotinylated antibodies can be extended to coat the internal surface of an intact bioreactor (that is, the bioreactor matrix plus the inlet and outlet).

Comparison of T Cells Incubated with Antibody-Coated Bioreactor Matrix and Magnetic Beads for T-cell Expansion An antibody-coated matrix (without inlet and outlet) was compared with the Miltenyi MACSiBead™ system. The magnetic beads (already coated with streptavidin) were coated with biotinylated anti-CD2, CD3, and CD28 antibodies according to the manufacturer's protocol, which is similar to the coating procedure described above. The relatively small 2.1 cm diameter by 0.7 cm height bioreactor (FIG. 7e), listed in Table 1, was used. The bioreactor matrix fits in a well of a 12-well plate so that one can easily compare the performance of beads and matrix. Three bioreactor matrices were coated with avidin or streptavidin first, and then the biotinylated CD2, CD3, CD28 antibodies using the preferred procedures described above. The same concentrations of antibodies were used to coat the bioreactor matrix and the MACSiBeads. One bioreactor matrix with streptavidin coating was not further coated with antibodies (the negative control)

Human peripheral blood CD3+ Pan T cells (ReachBio Research Labs) were first activated and expanded (7-day) using the MACSiBeads according to the manufacturer's protocol and then removed from the magnetic particles. Then $4.5 \times 10^6$ T cells were added to four wells of a 12-well plate, respectively. Four wells, each filled with 3 mL of culture medium (RPMI 1640 supplemented with 10% fetal bovine serum and 20 IU/mL of human IL2), contained either 1) $7.5 \times 10^6$ antibody-coated magnetic beads, 2) antibody-coated streptavidin-matrix, 3) antibody-coated avidin-matrix, and 4) streptavidin-matrix without antibody coating, respectively. Additional medium was added to the well on Day 3. On Day 5, the cells were divided into two wells with additional beads and matrices. The number of T cells in each well, after being dissociated from the magnetic beads or the matrix, were counted on Days 3, 5 and 7.

Figure 15:
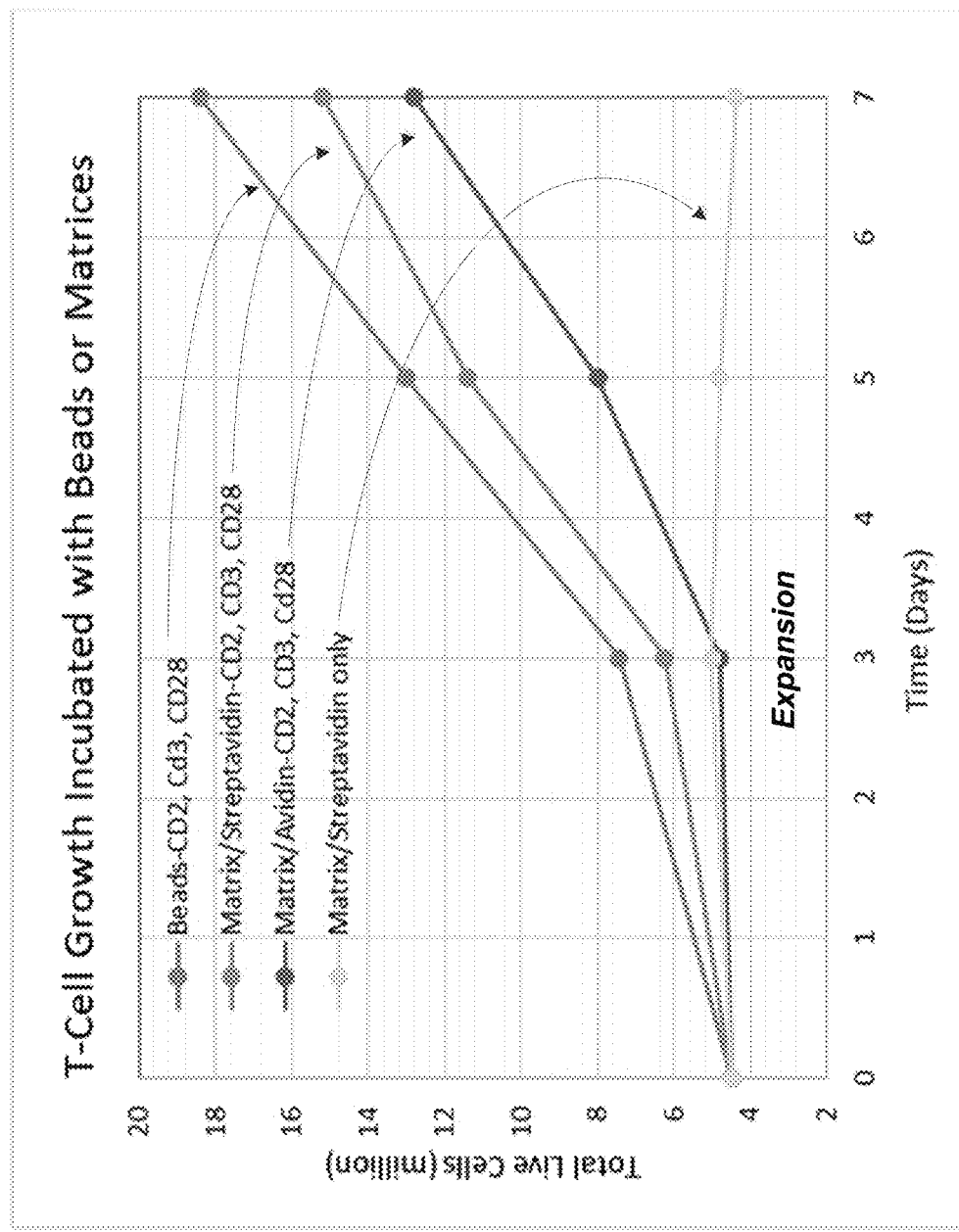
FIG. 15 illustrates T-cell growth (after beads activation) incubated (static) with antibody-coated magnetic beads and bioreactor matrix versus a bioreactor matrix without an antibody coating.

FIG. 15 shows T-cell growth (after activation) incubated with antibody-coated magnetic beads and matrices versus a matrix without an antibody coating. The trend of T cell growth in antibody coated-matrices is similar to that of antibody-coated beads. However, T cells incubated with the matrix without antibodies did not proliferate, probably due to the lack of continued stimulation. In this experiment, the matrix was placed in a well under static condition. Therefore, the results are expected to be different from the perfusion based bioreactor. This experiment clearly indicate that the antibodies were successfully coated on the bioreactor's matrix surfaces, and they promoted the T cell growth.

Figure 16:
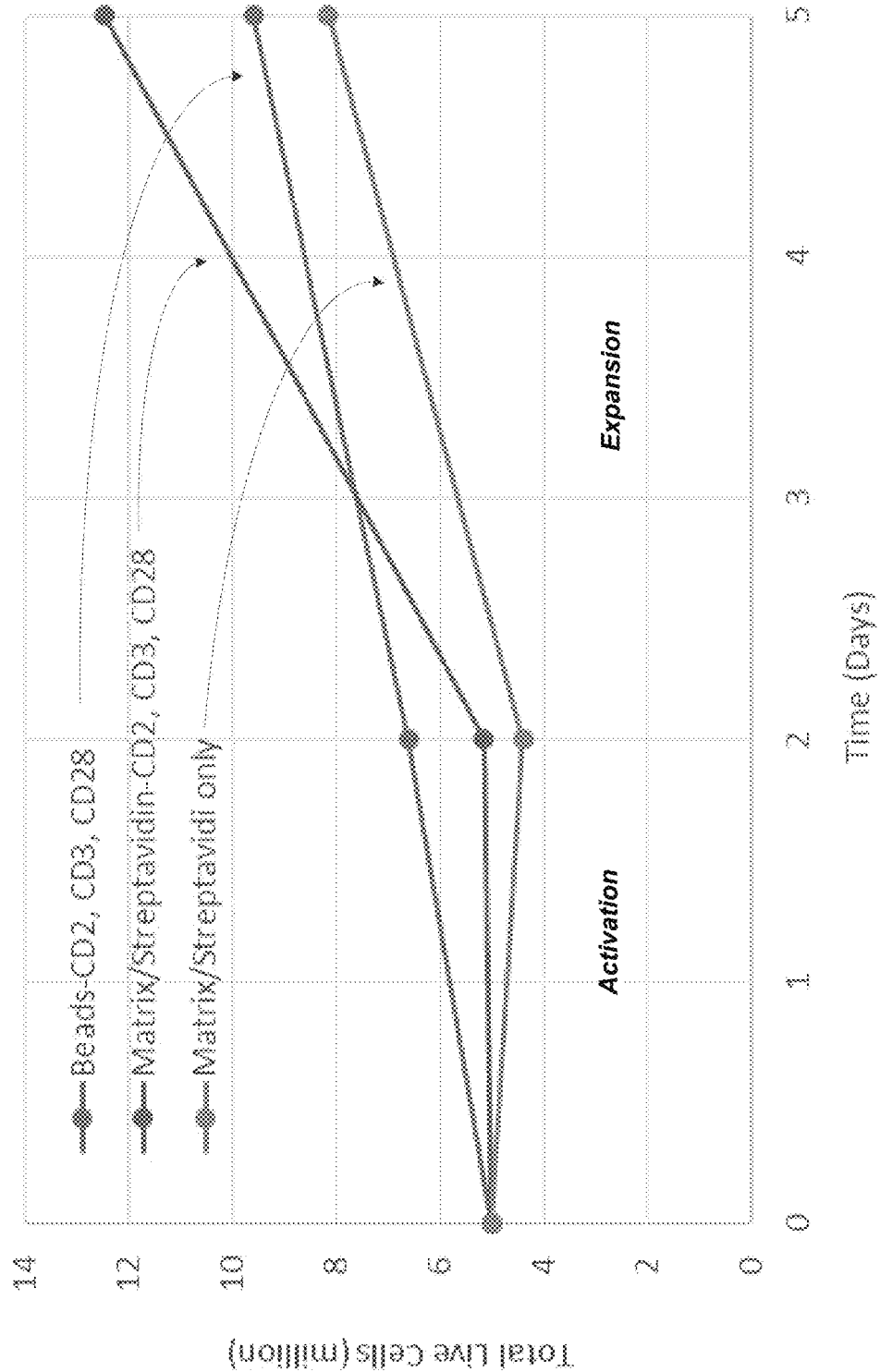
FIG. 16 illustrates T-Cell activation and expansion incubated (static) with beads, bioreactor matrix with antibody coating and bioreactor matrix without antibody coating, respectively.

Comparison of Peripheral Blood Mononuclear Cells (PBMCs) Incubated with Antibody-Coated Bioreactor Matrix and Magnetic Beads for Both T-Cell Activation and Expansion A similar study to the above was performed with PBMCs instead of isolated T-cells. Typically, PBMCs, which include T cells and other mononuclear such as B cells, NK cells, monocytes, were collected from a patient and directly used for cell expansion without T-cell isolation. This is because non-T cells will not be activated by CD2, CD3, and CD28, and they will be naturally eliminated after several days without activation. Another difference of this experiment from the experiment in FIG. 15 is the incorporation of the cytokine activation step when using the antibody-coated matrix. Briefly, 2 mL of culture medium containing PBMCs at density of $2.5 \times 10^6$ cells/mL were added to three wells of a 12-well plate. The three wells contain 1) $7.5 \times 10^6$ antibody-coated magnetic beads, 2) antibody-coated streptavidin-matrix, and 3) streptavidin-matrix without antibody coating, respectively. Avidin coated matrix was not used in this experiment as streptavidin has shown superior to avidin in the last two experiments. PBMCs were incubated in each well for two days for activation. Then additional media containing IL2 cytokine were added to the well so that the media has 20 IU/mL of human IL2 to start the expansion phase. The change of the total cell number during the 5-day culture is illustrated in FIG. 16. This confirms that the T-cells expanded with antibody-coated matrix resulted in more T cells when compared with antibody coated magnetic beads. This also confirms that the antibody-coated matrix can provide equivalent or better T-cell activation and expansion.

Dynamic Perfusion Based T-Cell Expansion

A perfusion-based 3D bioreactor was fabricated as described herein. The 3D bioreactor's internal surface was prepared by coating with polydopamine for 12 hours. The bioreactor internal surface was then coated with streptavidin for 12 hours. The bioreactor was then incubated with 70% ethanol for sterilization. After sterilization, the internal surface was washed with PBS and coated with an equal mixture of CD2, CD3, and CD28-Biotin conjugates (10 μg/mL concentration for each antibody) to immobilize antibodies on the bioreactor's internal surfaces using the procedure described above.

A perfusion circuit was set up as illustrated in FIG. 12. A Masterflex L/S with Cytoflow pump head (Cole-Parmer), which is designed for pumping live cells and shear-sensitive fluids, was used for the perfusion system. As this application uses a relatively small bioreactor and the perfusion rate is expected to be relatively low, a custom-built oxygenation unit using gas diffusion into the medium and medium droplets was employed instead of an oxygenator.

Figure 17:
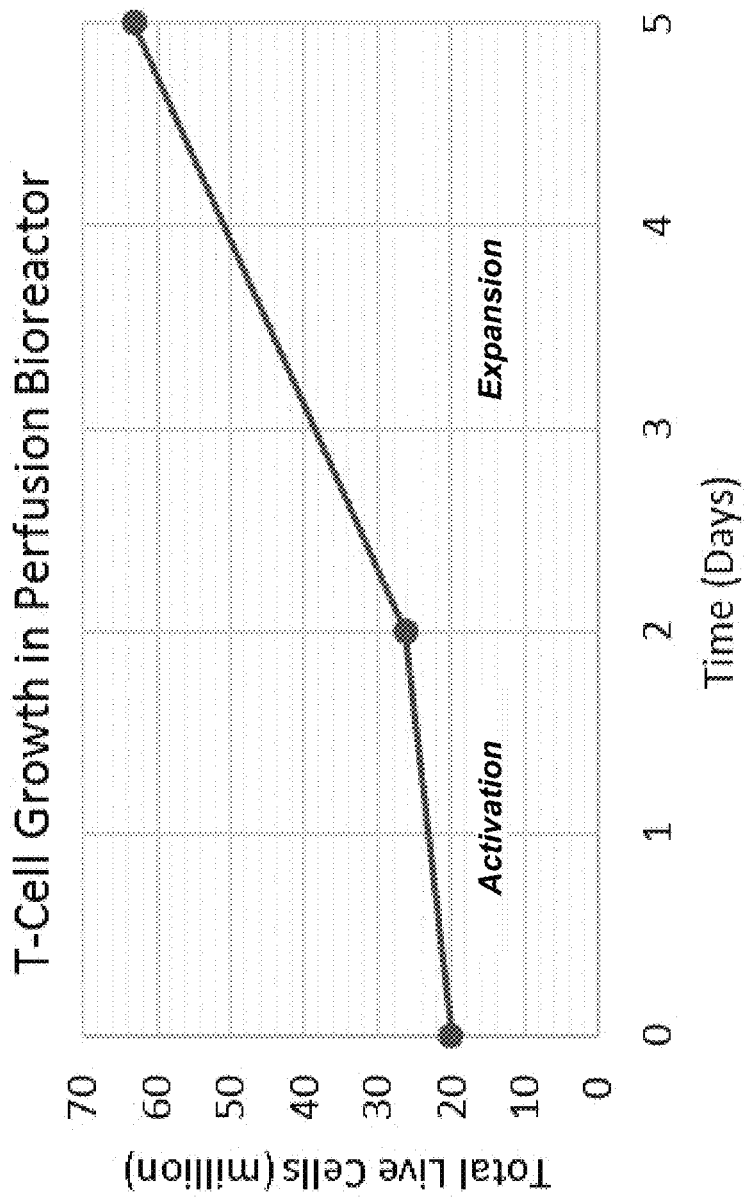
FIG. 17 illustrates T-cell activation and expansion in a 3D bioreactor with continuous perfusion.

About $20 \times 10^6$ PBMCs were seeded into the primed bioreactor perfusion system. The cells were distributed evenly by circulating for 15 minutes at 2 mL/min. During the activation phase, (the perfusion medium containing no cytokine IL2 promoter), the T-cells were perfused at the rate of 0.1 mL/min on Day 1 and 0.14 mL/min on Day 2. After two days of activation, cell density was determined and media with human IL-2 cytokine was added to the system so that the total IL-2 concentration was 20 IU/mL. The T-cell expansion phase was carried out for 3 days at a perfusion rate of 0.2 mL/min. The cell density was determined on day 5 and the results are shown in FIG. 17. Similar to the static experiment shown in FIGS. 15 and 16, T cells achieved a three-fold of expansion after activation/promotion.

Ozone/UV Surface Treatment of Parylene C Coated 3D Bioreactor

As noted above, the parylene coatings may be functionalized. By way of example, in the case of a parylene C coated bioreactor herein, such was treated with an ultraviolet/ozone system, which is contemplated to provide hydroxyl, carbonyl and carboxylate surface groups. More specifically, the 3D bioreactor was placed in a closed chamber with UV transparent glass on one side. A UV lamp (254 nm) is placed above the glass about 1.75" in distance to yield a 3.2 mW/cm$^2$ exposure flux applied simultaneously during ozone exposure. The inlet of the closed chamber was connected to a VMUS-4 ozone generator (Azco Industries) through PTFE tubing and the outlet of the closed chamber was connected to a glass bottle filled with mineral oil, all within a fume hood. The ozone generator was set at 2 L/min inlet flow of air. The output was set to an efficiency of 100% to deliver about 2.5 g of ozone per hours. Parylene C coated bioreactors were ozone treated for 1, 2, 5, 10 and 15 minutes, respectively. As can be seen from the Table 3 blow, treating the parylene C surface for 10 minutes made the surface as hydrophilic as a polydopamine/fibronectin (PD/FB) treated surface. See U.S. patent application Ser. No. 15/585,812 the teachings of which are incorporated herein by reference.

TABLE 3

Effects Of Coating Procedure On Water Contact Angle

| Surface Treatment | Water Contact Angle |
|---|---|
| Parylene C coated bioreactor | 73.7 ± 9.5 |
| Polydopamine/fibronectin | 44.0 ± 9.5 |
| Ozone/UV 1 min | 64.7 ± 6.0 |
| Ozone/UV 2 min | 53.0 ± 5.0 |
| Ozone/UV 5 min | 51.0 ± 3.5 |
| Ozone/UV 10 min | 41.7 ± 3.1 |
| Ozone/UV 15 min | 34.7 ± 4.0 |

Figure 19:
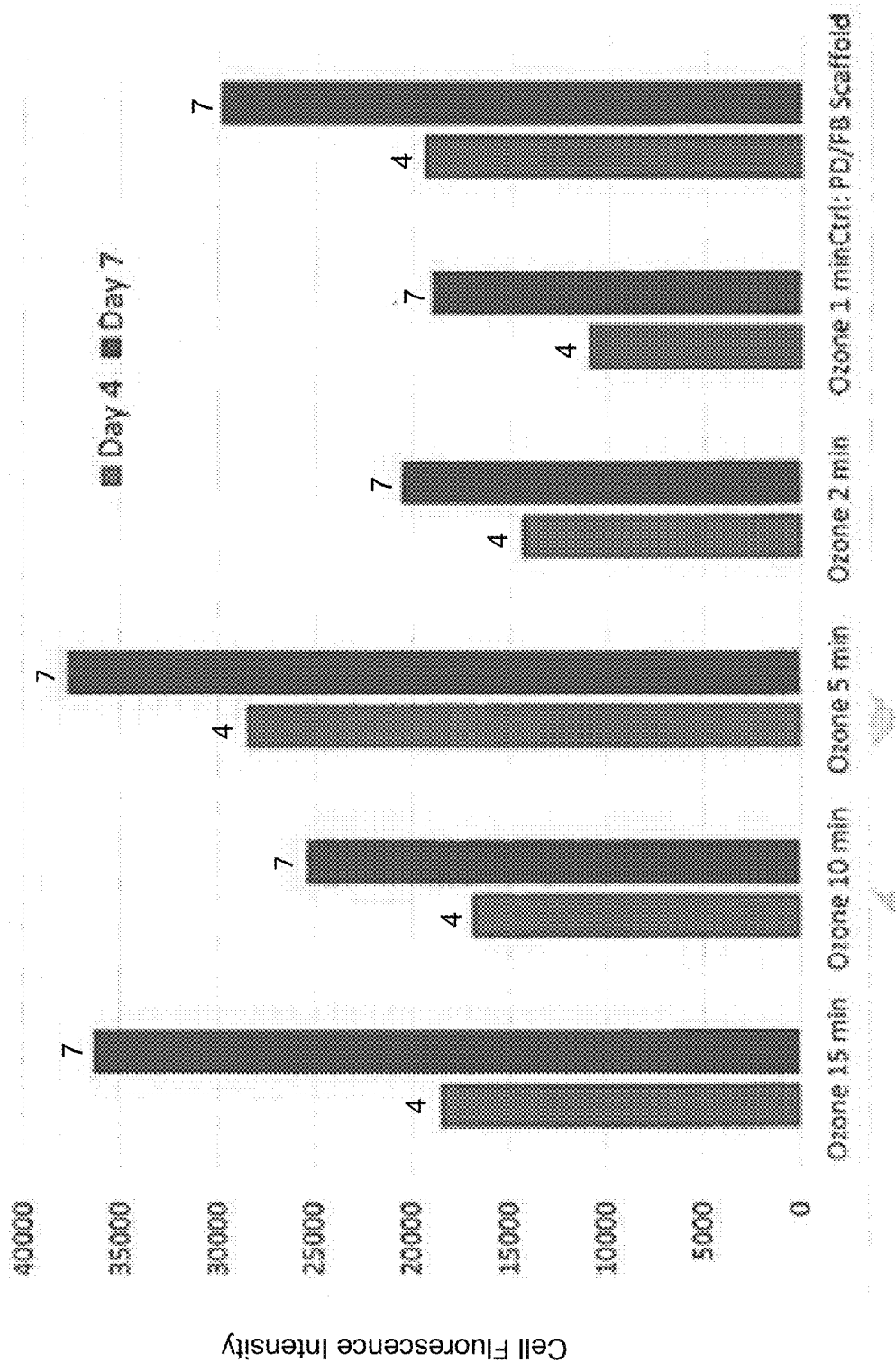
FIG. 19 shows the comparative results of a parylene C coated 3D bioreactor with different lengths of UV/ozone treatment.
Figure 20:
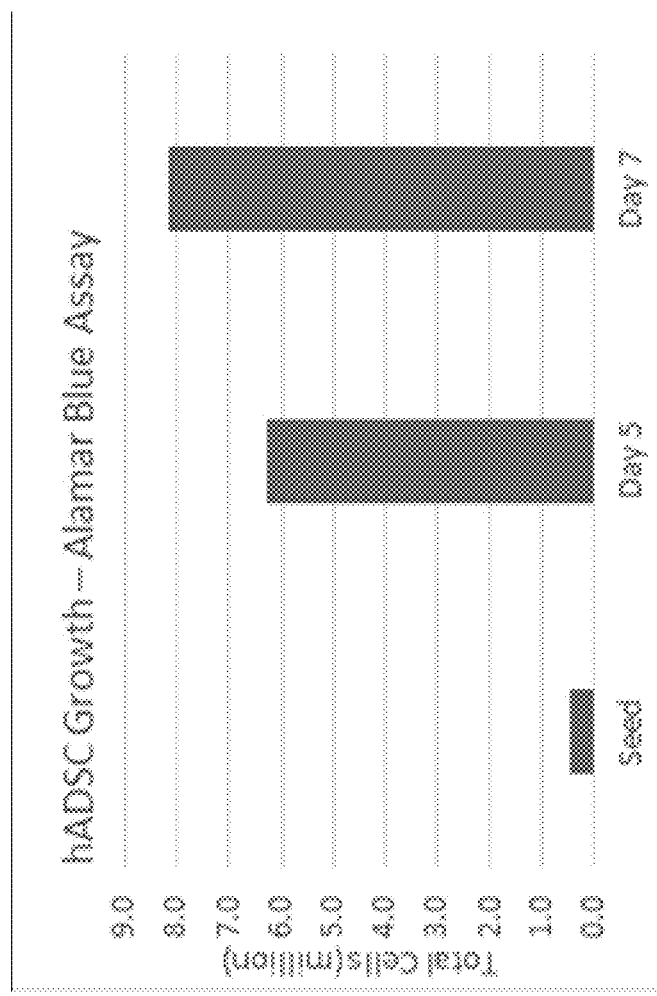
FIG. 20 shows cell expansion human derived adipose stem cells (hADSC) on a parylene C coated 3D bioreactor with UV/ozone treatment.
Figure 21:
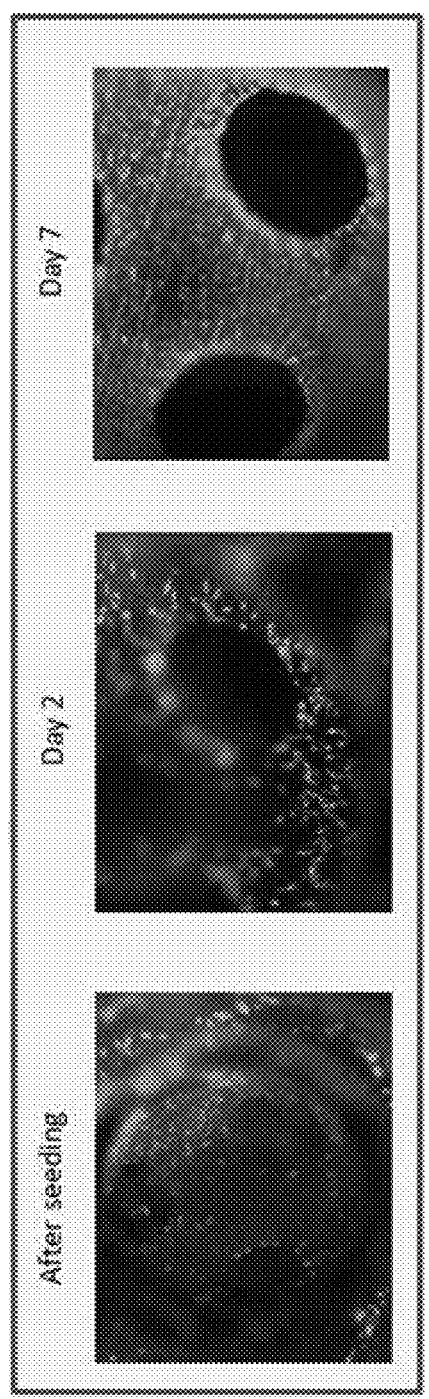
FIG. 21 shows fluorescence microscopic images showing increasing number of living ADSC cells as a function of time in the 3D bioreactor.

FIG. 19 shows that UV/ozone treating the parylene C coating on the bioreactor for 5 min was optimal for cell multiplication of adherent mesenchymal stem cells (MSC) that had been previously seeded on the bioreactor. Increase in fluorescence intensity using a MTT assay is a result of increasing numbers of cells. The cell multiplication at this exposure exceeded even that achieved by the polydopamine and fibronectin coated bioreactor for both 4 and 7 days. This indicates that the relatively more complex PD/FB treatment is unnecessary. FIG. 20 shows cell expansion of human derived adipose stem cells (hADSC). FIG. 21 shows the corresponding fluorescence microscope images showing increasing number of ADSC cells as a function of time in the 3D bioreactor.

Sterilization and Packaging

It is contemplated herein that in lieu of gamma radiation sterilization of the 3D bioreactors herein, that may now contain parylene film type coatings, sterilization may rely upon perfused chlorine dioxide (ClO$_2$) gas prior to antibody surface immobilization in the case of non-adherent T-cell expansion. The ClO$_2$ gas is not contemplated to react with a functionalized parylene film coating (i.e. —Cl, —CHO, —COOH, —NH$_2$ or —C(O)CF$_3$) or the underlying 3D bioreactor polymer substrate.

For example, the 3D bioreactor herein may now be sealed in a polymeric film which may then be placed in an atmosphere of chlorine dioxide for the purpose of sterilization. Subsequently, such sterilized 3D bioreactors would be exposed to a flowing air stream to release any remaining chlorine dioxide gas. Additional methods of sterilization include steam, ozone, hydrogen peroxide, sulfur dioxide and/or ethylene oxide sterilization.

What is claimed is:

1. A 3D bioreactor for growth of cells comprising a plurality of voids having a surface area for cell expansion, said plurality of voids having a diameter D, a plurality of pore openings between said voids having a diameter d, such that D>d and wherein: (a) 90% or more of said voids have a selected void volume (V) that does not vary by more than +/−10.0%; and (b) 90% or more of said pore openings between said voids have a value of d that does not vary by more than +/−10.0%; wherein said bioreactor has a coating of a substituted or unsubstituted poly(p-xylylene) and polydopamine is applied to said poly(p-xylylene) coating wherein said polydopamine is capable of binding an additional layer or layers for cell culturing.

2. The 3D bioreactor of claim 1 wherein said bioreactor contains 0.01% by weight to 0.25% by weight of material having a MW of less than or equal to 500.

3. The 3D bioreactor of claim 1 wherein said poly(p-xylylene) has the following structure,

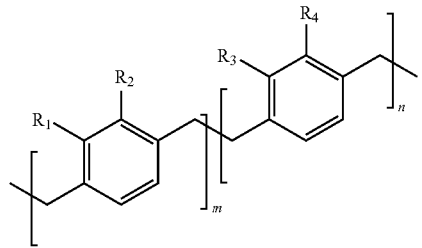

wherein R$_1$, R$_2$, R$_3$, and R$_4$ are selected from hydrogen, a halogen, amine (—NH$_2$), aliphatic aldehyde (—CHO), carboxylic acid functionality (—COOH), hydroxyl (—OH) or carboxylate functionality comprising —C(O)CF$_3$.

4. The 3D bioreactor of claim 1 wherein said coating has a thickness of 200 Angstroms to 100.0 μm.

5. The 3D bioreactor of claim 1 wherein said poly(p-xylylene) coating comprises a plurality of coating layers having different chemical composition.

6. The 3D bioreactor of claim 3 wherein said substituted poly(p-xylylene) coating is bonded to a poly(ethylene oxide) which includes a terminally substituted antibody protein.

7. The 3D bioreactor of claim 3 wherein at least one of R$_1$, R$_2$, R$_3$, and R$_4$ are selected from an aldehyde (—CHO) and said 3D bioreactor is bonded to a poly(ethylene oxide) having a terminally substituted antibody protein, via a linkage having the following structure: —CH=N—.

8. The 3D bioreactor of claim 1 further including an extracellular matrix protein attached to said polydopamine coating.

9. The 3D bioreactor of claim 1 further including a tetrameric protein attached to said polydopamine coating.

10. The 3D bioreactor of claim 9 further including a biotinylated antibody immobilized on said tetrameric protein.

11. The 3D bioreactor of claim 9 wherein said tetrameric protein comprises avidin or streptavidin.

12. The 3D bioreactor of claim 10 wherein said biotinylated antibody comprises anti-CD-3 antibody.

13. The 3D bioreactor of claim 10 wherein said biotinylated antibody comprises anti-CD3 antibody and anti-CD28 antibody.

14. The 3D bioreactor of claim 10 wherein said biotinylated antibody comprises anti-CD3 antibody, anti-CD28 antibody and anti-CD2 antibody.

15. A method of forming a 3D bioreactor comprising:
forming said 3D bioreactor by additive manufacturing wherein said 3D bioreactor includes a plurality of voids having a surface area for cell expansion, said plurality of voids having a diameter D, a plurality of pore openings between said voids having a diameter d, such that D>d and wherein: (a) 90% or more of said voids have a selected void volume (V) that does not vary by more than +/−10.0%; and (b) 90% or more of said pore openings between said voids have a value of d that does not vary by more than +/−10.0%; and
coating said bioreactor with substituted or unsubstituted poly(p-xylylene) and applying polydopamine to said poly(p-xylylene) coating wherein said polydopamine is capable of binding an additional layer or layers for cell culturing.

16. The method of claim 15 wherein said additive manufacturing comprises stereolithography (SLA) or digital light processing (DLP).

17. The method of claim 16 wherein said bioreactor, prior to coating with substituted or unsubstituted poly(p-xylylene), is exposed to UV light.

18. The method of claim 16 wherein said bioreactor, prior to coating with substituted or unsubstituted poly(p-xylylene), is exposed to vacuum.

19. The method of claim 16 wherein said bioreactor, prior to coating with substituted or unsubstituted poly(p-xylylene), is exposed to heating.

20. The method of claim 15 wherein said substituted or unsubstituted poly(p-xylylene) coating is exposed to UV light and ozone.

* * * * *